US012674133B2

(12) United States Patent　　　　(10) Patent No.:　US 12,674,133 B2
Gilligan et al.　　　　　　　　　　　(45) Date of Patent:　　Jul. 7, 2026

---

(54) METHODS FOR SEX-SORTING SPERM

(71) Applicant: Inguran, LLC, Navasota, TX (US)

(72) Inventors: Thomas B. Gilligan, College Station, TX (US); Kenneth Michael Evans, College Station, TX (US)

(73) Assignee: Inguran, LLC, Navasota, TX (US)

( * ) Notice: Subject to any disclaimer, the term of this patent is extended or adjusted under 35 U.S.C. 154(b) by 331 days.

(21) Appl. No.: 16/815,951

(22) Filed: Mar. 11, 2020

(65) Prior Publication Data

US 2020/0291351 A1　　Sep. 17, 2020

Related U.S. Application Data

(60) Provisional application No. 62/817,135, filed on Mar. 12, 2019.

(51) Int. Cl.
| | |
|---|---|
| *C12N 5/071* | (2010.01) |
| *C12N 5/076* | (2010.01) |
| *G01N 33/50* | (2006.01) |

(52) U.S. Cl.
CPC ........... *C12N 5/0612* (2013.01); *C12N 5/061* (2013.01); *G01N 33/5044* (2013.01)

(58) Field of Classification Search
CPC ... C12N 5/0612; C12N 5/061; G01N 33/5044
See application file for complete search history.

(56) References Cited

U.S. PATENT DOCUMENTS

| | | | | |
|---|---|---|---|---|
| 5,135,759 | A | 8/1992 | Johnson | |
| 7,012,689 | B2 * | 3/2006 | Sharpe | G01B 11/00 356/399 |
| 2007/0117086 | A1 * | 5/2007 | Evans | C12Q 1/00 435/4 |
| 2012/0225418 | A1 * | 9/2012 | Meyer | A01N 1/02 435/2 |
| 2016/0010057 | A1 | 1/2016 | Vishwanath | |

FOREIGN PATENT DOCUMENTS

| | | |
|---|---|---|
| EP | 2914712 B1 | 10/2013 |
| EP | 2914712 A2 | 9/2015 |
| WO | 2001/85913 A2 | 5/2001 |
| WO | 2004017041 A2 | 2/2004 |
| WO | 2004/104178 A2 | 12/2004 |
| WO | 2005/095960 A1 | 3/2005 |
| WO | 2011/123166 A2 | 12/2010 |
| WO | 2013/049631 A1 | 9/2012 |
| WO | 2014/035840 A1 | 9/2012 |
| WO | 2016/090310 A1 | 12/2015 |
| WO | 2019018609 A1 | 1/2019 |

OTHER PUBLICATIONS

Donoghue et al., Effects of water- and lipid-soluble antioxidants on Turkey sperm viability, membrane integrity, and motility during liquid storage, Poultry Science, 76: 1440-1445, (Year: 1997).*

Suh et al. High pressure flow cytometric sorting damages sperm, Theriogenology, 64: 1035-1048. (Year: 2005).*
Kasimanickam et al. Effect of breed and sperm concentration on the changes in structural, functional and motility parameters of ram-lamb spermatozoa during storage at 4 degrees C, Animal Reproduction Science, 101: 60-73 (Year: 2007).*
Fan et al. High throughput and parallel flow cytometer using microball lens integrated 3D microfluidic device, Proceedings of the 12th IEEEE international Conference on Nano/Micro Engineered and Molecular Systems, p. 426-429. (Year: 2017).*
BD Bioscience, Introduction to Flow Cytometry: A Learning Guide, Chapters 1 and 2, Becton, Dickinson and Company. (Year: 2002 ).*
Merriam-Webster, definition "interrogate", retrieved from internet Sep. 2, 2022. (Year: 2022).*
Steinkamp et al., Flow cytometry, Rev. Sci. Instrum., 55(9): 1375-1400. (Year: 1984).*
Vishwanath et al., Review: Semen sexing—current state of the art with emphasis on bovine species, Animal, 12(S1): s85-s96. (Year: 2018).*
BD Biosciences, BD FACSAria II Technical Specification. (Year: 2011).*
Funaro et al., A novel sorting technology allows for highly efficient selection of sperm without chromatin damage, Systems Biology in Reproductive Medicine, 59(3): 172-177. (Year: 2013).*
Arnold et al., Practical Issues in High-Speed Cell Sorting, Unit 1.24, Current Protocols in Cytometry 1.24.1-1.24.30 (Year: 2010).*
Canadian Office Action issued on Oct. 20, 2022 in related CA Appl. No. 3,132,979.
Supplementary European Search Report issued on Jan. 12, 2022 in related EP Appl. No. 20770568.2.
EPO Third Party Observations filed on Oct. 17, 2023 in related EP Application No. 20770568.2.
Keij et al. "High-Speed Photodamage Cell Sorting: An Evaluation of the Zapper Prototype." Methods of Cell Biology. vol. 42, p. 371-386. 1994.
Canadian Office Action issued on Nov. 17, 2023 in related CA Application No. 3,132,979.
EP Examination Report issued Dec. 6, 2023 in related EP Application No. 20 770 568.2 filed on Sep. 10, 2021.
European Examination Report issued Aug. 12, 2024, in related EP Appl No. 20770568.2, filed on Sep. 10, 2021.
Keij J F et al. "High-speed photodamage cell sorting: an evaluation of the Zapper prototype." Cytometry: Part B, vol. 42, Jan. 1, 1994 (Jan. 1, 1994), pp. 371-386, XP009144703.
Office Action issued in counterpart European Application No. 20770568.2, dated May 14, 2025 (12 pages).

* cited by examiner

*Primary Examiner* — James D Schultz
*Assistant Examiner* — Joseph Paul Miano
(74) *Attorney, Agent, or Firm* — Ryan Christensen; Hashim Rahman

(57) ABSTRACT

The invention comprises depletive methods of sex-sorting sperm at high event rates, while simultaneously achieving high technical yields.

11 Claims, 7 Drawing Sheets

10

METHODS FOR SEX-SORTING SPERM

REFERENCE TO RELATED APPLICATIONS

This application claims the benefit of U.S. Provisional Patent Application No. 62/817,135 filed Mar. 12, 2019. The entire disclosure of which is incorporated herein by reference.

BACKGROUND OF THE INVENTION

Sperm sorting for sex selection (i.e., sex-sorting) via flow cytometry was scientifically established nearly 30 years ago (see Johnson, et. al.). Today, a portion of the global market for livestock artificial insemination (primarily dairy cattle) encompasses the use of sex-sorted sperm, typically having sex purities of 85% or higher. However, prior art sex-sorting methods typically only recover about 25% of the processed sperm, while discarding the remaining 75% of sperm. Those losses, when applied to sires with high genetic merit, represent a significant amount of "genetic potential" that is lost, i.e., the number of progeny born from such high value sires is reduced by the use of sex-sorted sperm. Additionally, for swine in particular, the need for large insemination doses has greatly limited the use of sex-sorted sperm due to the low yields associated with prior art sorting methods.

The main alternative to sex-sorted sperm is conventional (i.e., unsorted) sperm, which generally has a sex purity of about 50%. Conventional sperm still dominates the artificial insemination market in livestock, due in large part to the aforementioned inefficiencies of the sex-sorting process. Accordingly, there is an unmet need for a sperm sorting method that can provide sex purities higher than 50% (e.g., 55-65%) while utilizing high sort rates and simultaneously achieving high technical yields.

SUMMARY OF THE INVENTION

One embodiment of the invention comprises a method of producing a subpopulation of sperm enriched for a desired sex chromosome comprising: generating a stream containing a population of sperm; interrogating the population of sperm with a source of electromagnetic radiation; detecting signals produced in response to interrogation with the source of electromagnetic radiation; identifying sperm in the population of sperm that do not have the desired sex chromosome based on the detected signals; removing the identified sperm from the population of sperm to form a subpopulation of sperm enriched for the desired sex chromosome; and collecting the subpopulation of sperm.

Another embodiment of the invention comprises a method of producing a subpopulation of sperm enriched for a desired sex chromosome comprising: generating a stream containing a population of sperm; interrogating the population of sperm with a source of electromagnetic radiation; detecting signals above a threshold value at an event rate, wherein the signals are produced in response to interrogation with the source of electromagnetic radiation; identifying sperm in the population of sperm that do not have the desired sex chromosome based on the detected signals; perturbing the stream into regularly formed drops at a drop drive rate, wherein the event rate is between 85 percent and 150 percent of the drop drive rate; removing the identified sperm from the population of sperm to form a subpopulation of sperm enriched for the desired sex chromosome; and collecting the subpopulation of sperm.

Additional embodiments of the invention require the additional steps of: identifying dead, dying or damaged sperm based on the detected signals; and removing the identified dead, dying or damaged sperm from the population of sperm.

In a further embodiment of the invention, a collected subpopulation enriched for the desired sex chromosome is collected at a rate of: between about 20,000 sperm per second and 25,000 sperm per second; between about 25,000 sperm per second and about 30,000 sperm per second; between about 30,000 sperm per second and about 35,000 sperm per second; between about 35,000 sperm per second and about 40,000 sperm per second; between about 40,000 sperm per second and about 45,000 sperm per second; between about 45,000 sperm per second and about 50,000 sperm per second; between about 50,000 sperm per second and about 55,000 sperm per second; between about 55,000 sperm per second and about 60,000 sperm per second; between about 60,000 sperm per second and about 65,000 sperm per second; between about 65,000 sperm per second and about 70,000 sperm per second; between about 70,000 sperm per second and about 75,000 sperm per second; and between about 75,000 sperm per second and about 80,000 sperm per second.

In an even further embodiment, a step of removing identified sperm from a population of sperm comprises the charged deflection of drops formed from a stream in which the identified sperm are located, wherein said drops are regularly formed at a drop drive rate.

In a yet further embodiment of the invention, a step of removing identified sperm comprises deflecting all droplets expected to contain identified sperm, regardless of whether additional sperm is present in the droplet. In an alternative embodiment, a step of removing identified sperm comprises only deflecting droplets expected to contain identified sperm, and no other sperm, within the droplet.

In a specific embodiment of the invention, the purity of the subpopulation of sperm enriched for a desired sex chromosome is between about 55% and about 70%. In an even more specific embodiment, the purity of the subpopulation of sperm enriched for a desired sex chromosome comprises: between about 55% and about 60%; between about 60% and about 65%; or between about 65% and about 70%.

In an additional embodiment of the invention, a step of collecting a subpopulation of sperm enriched for a desired sex chromosome comprises collecting the subpopulation in a collector.

Another aspect of the invention comprises an insemination dosage comprising sperm from a subpopulation of sperm enriched for a desired sex chromosome by any of the methods of the invention.

In yet another embodiment of the invention, the desired sex chromosome comprises the X chromosome. In an alternative embodiment, the desired sex chromosome comprises the Y chromosome.

In a further embodiment, a collected subpopulation of sperm enriched for the desired sex chromosome comprises between about 40% and about 45%, about 45% and about 50%, about 50% and about 55%, about 55% and about 60%, about 60% and about 65%, about 65% and about 70%, about 70% and about 75%, or about 75% and about 80%, of the population of sperm.

In yet another embodiment of the invention, a population of sperm is processed prior to a step of generating a stream by removing dead, dying or damaged sperm from the population. In a further embodiment, the population of sperm is treated with an antioxidant prior to the step of generating a stream.

An additional embodiment further comprises the step of establishing a gate for sperm that do not have the desired sex chromosome. In a further embodiment, the gate comprises between 35% and 55% of the population of sperm.

In another embodiment of the invention, detected signals above a threshold value are detected at an event rate. A further embodiment, comprises the step of perturbing a stream into regularly formed drops at a drop drive rate, wherein the event rate is between 85 percent and 150 percent of the drop drive rate.

In a specific embodiment of the invention, a subpopulation of sperm enriched for a desired sex chromosome is collected at a rate of at least 20,000 sperm per second, and wherein between 40 and 80 percent of the population of sperm are collected.

Another embodiment of the invention further comprises the step of collecting identified sperm removed from a population of sperm.

A yet further embodiment comprises the step of concentrating a population of sperm to a concentration of $200 \times 10^6$ to $400 \times 10^6$ sperm per ml prior to a step of generating a stream.

DETAILED DESCRIPTION OF THE INVENTION

Figure 1:
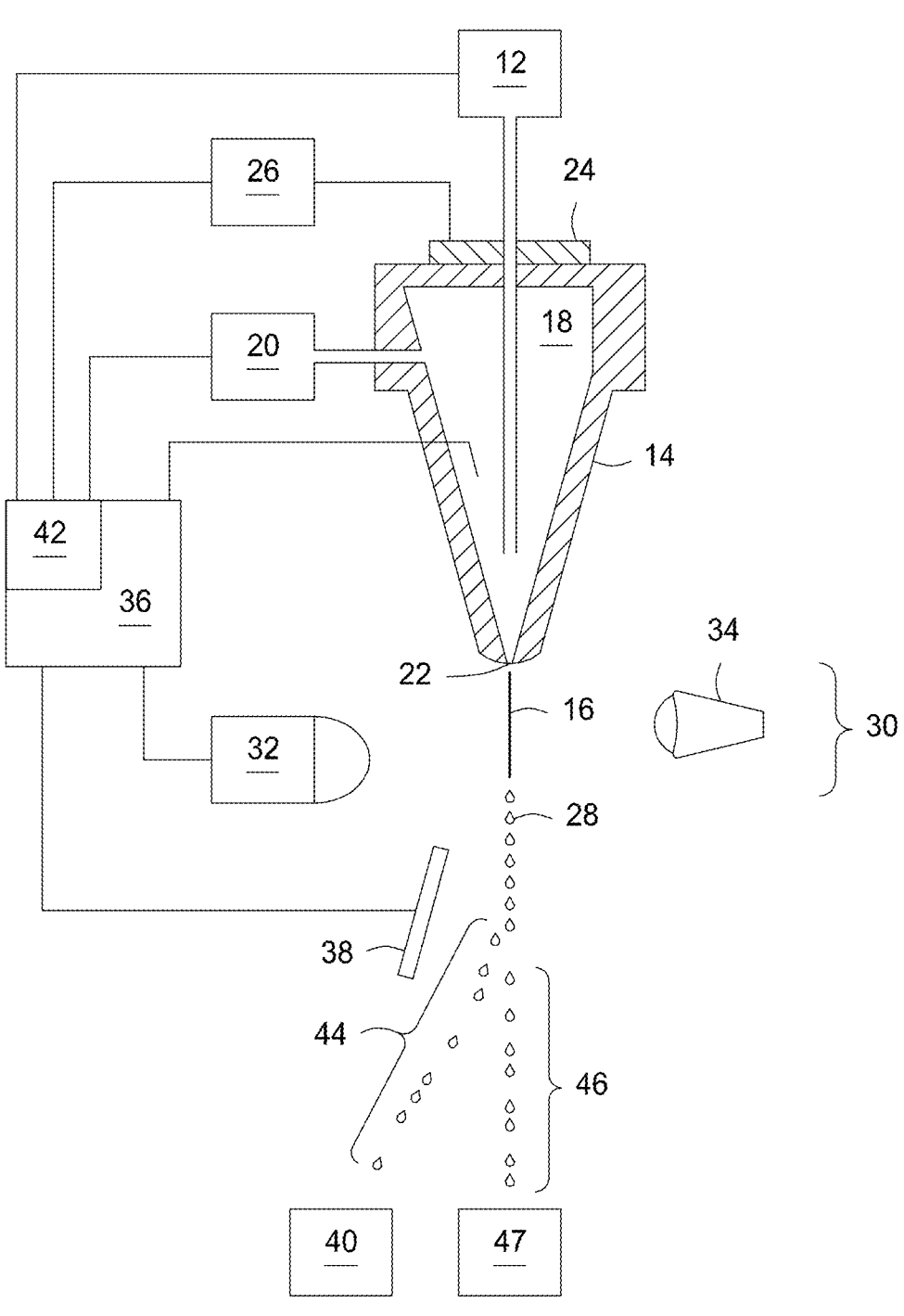
FIG. 1 is a depiction of a jet-in air flow cytometer used in connection with a method of the invention.
Figure 2:
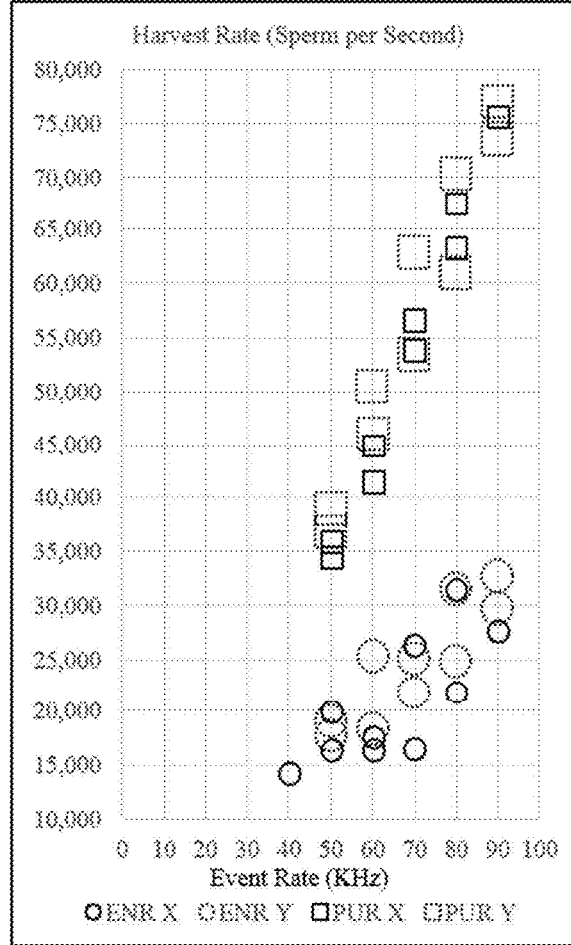
FIG. 2 is a graph showing sperm collection rates achieved with the invention when X is the desired sex chromosome and when Y is the desired sex chromosome.
Figure 3:
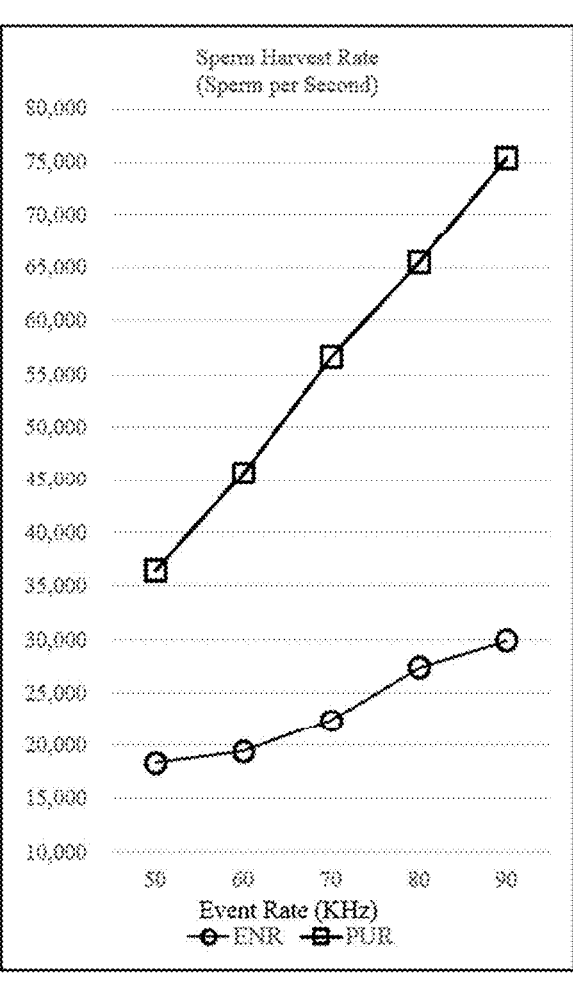
FIG. 3 is a graph showing sperm collection rates achieved with the invention when using enrich and purify sort modes.
Figure 4:
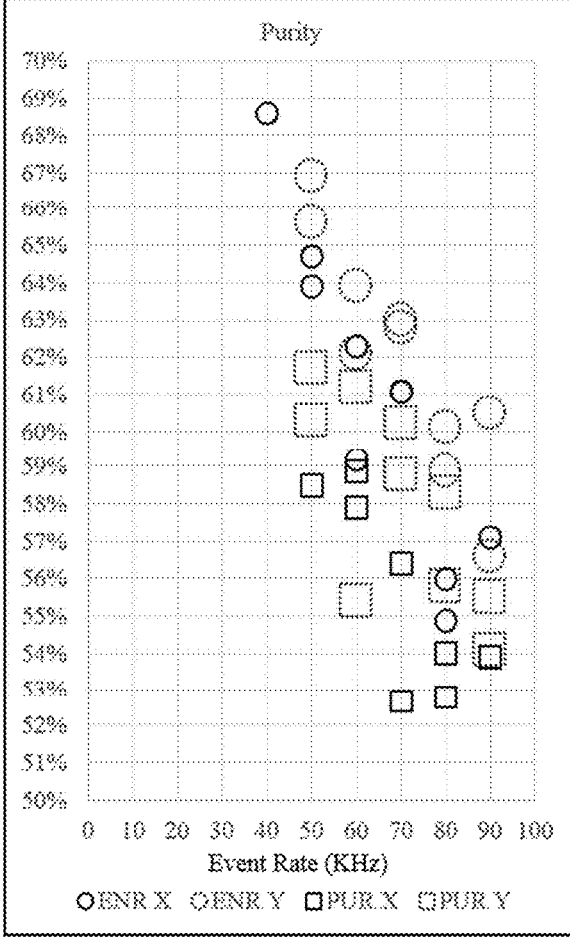
FIG. 4 is a graph showing sex chromosome purity achieved with the invention when X is the desired sex chromosome and when Y is the desired sex chromosome.
Figure 5:
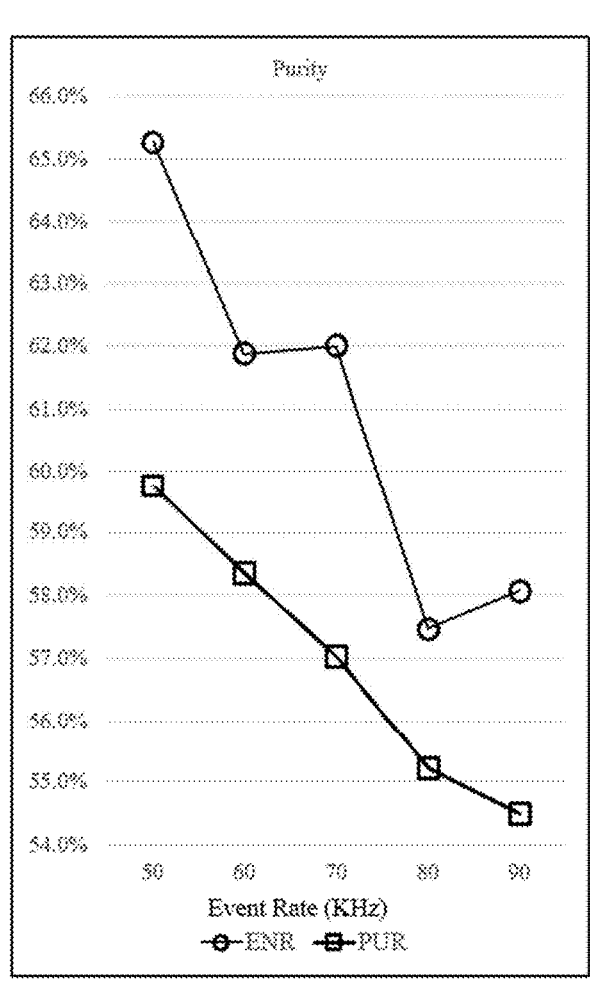
FIG. 5 is a graph showing sex chromosome purity achieved with the invention when using enrich and purify sort modes.
Figure 6:
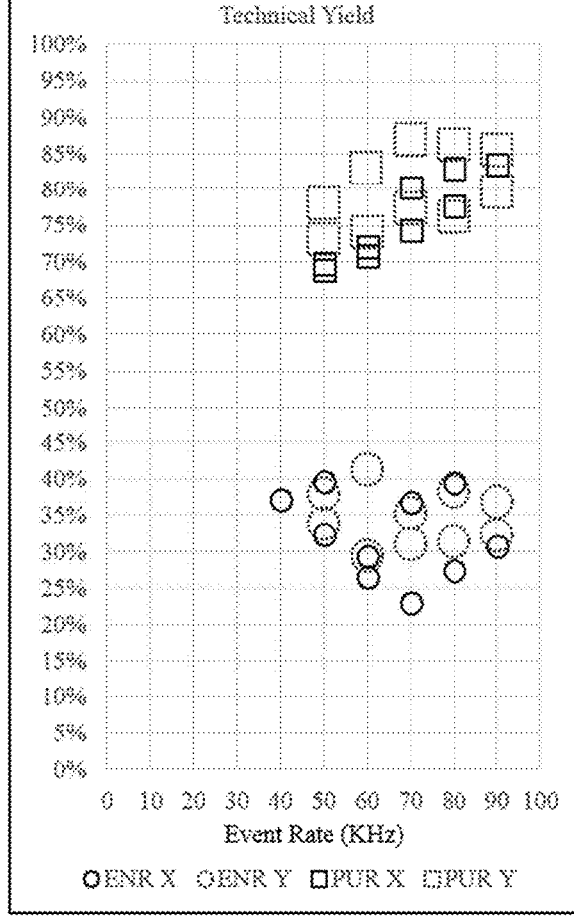
FIG. 6 is a graph showing technical yields achieved with the invention when X is the desired sex chromosome and when Y is the desired sex chromosome.
Figure 7:
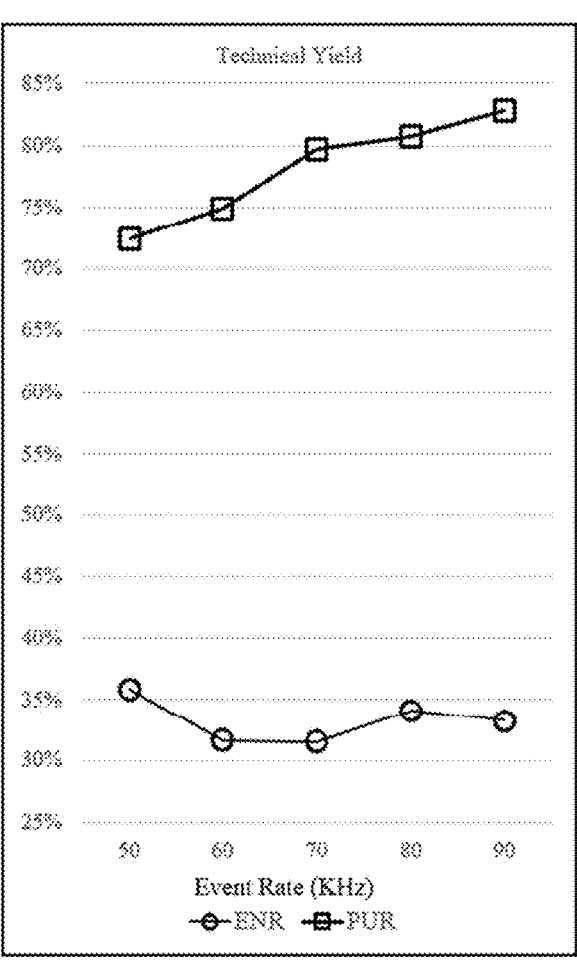
FIG. 7 is a graph showing technical yields achieved with the invention when using enrich and purify sort modes.
Figure 8:
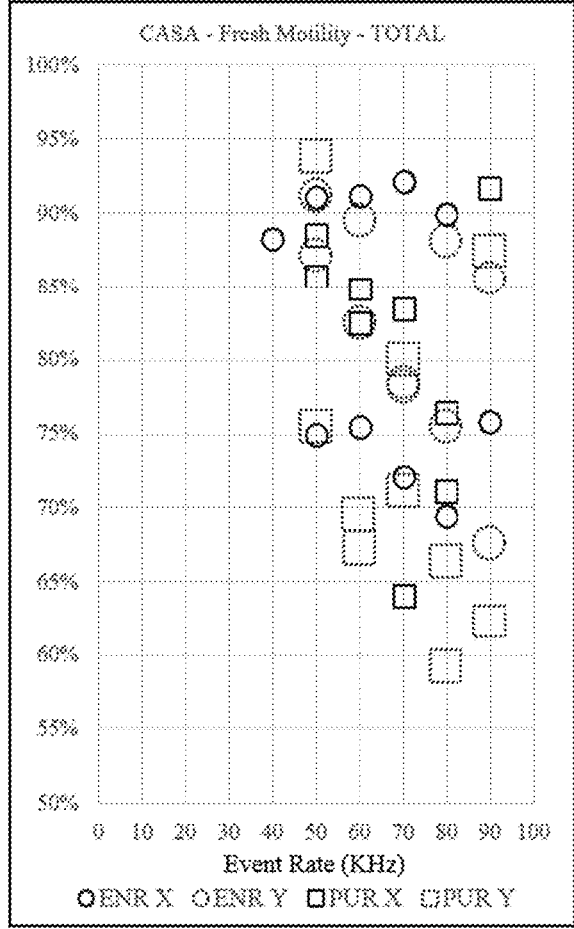
FIG. 8 is a graph showing motility of collected sperm achieved with the invention when X is the desired sex chromosome and when Y is the desired sex chromosome.
Figure 9:
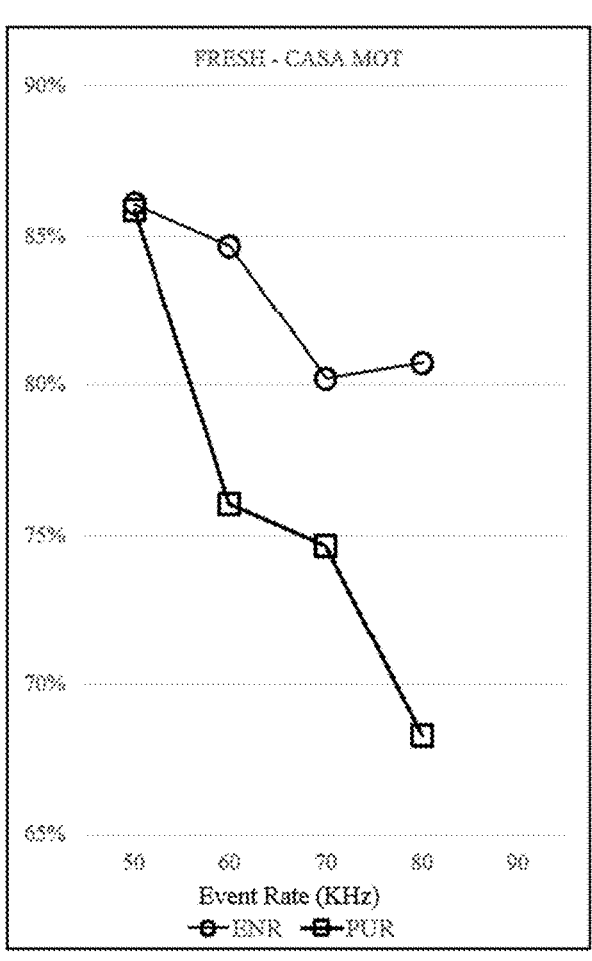
FIG. 9 is a graph showing motility of collected sperm achieved with the invention when using enrich and purify sort modes.

One aspect of the invention encompasses the use of a "high event rate" sorting method having an event rate to drop drive rate ratio ("ER/DDR ratio") greater than 0.85, and in some embodiments as high as 1.25, or higher. In flow cytometry, an "event" generally constitutes a detected signal that exceeds a threshold value. In the context of sex-sorting sperm specifically, the signals in question are produced in response to interrogation of sperm stained with a DNA-selective dye by a source of electromagnetic radiation, such as a laser. "Event rate" then, generally constitutes the number of detected signals that exceed the threshold value per second. In flow cytometers employing droplet sorting, "drop drive rate," or drop drive frequency, is the number of drops formed per second. Typically, in droplet sorters, droplets are formed by subjecting a stream to vibrations produced by a piezoelectric or electromagnetic transducer. The wavelength (i.e., droplet spacing), λ, the frequency of the applied vibration, f, and the velocity of the stream are related to each other according to the following equation: $v = f \times \lambda$. Thus, in order to maintain a specific droplet spacing, as droplet frequency is increased, stream velocity must also be increased. In accordance with Bernoulli's equation, in order to increase the velocity of a stream in a flow cytometer, all else remaining the same, fluid pressure must be increased.

In "selective" sorting, desired cells (i.e., target cells or cells of interest) are identified, removed from the population of cells and then collected for use, while the remaining population of cells is considered waste. In contrast to selective sorting, one aspect of the invention encompasses the use of "depletive" or "inverse" sorting. In inverse sorting, undesired cells are identified, removed from the population of cells, and then sent to waste, while the remaining population of cells is collected for use. In the context of the invention, instead of the selective sorting method in which subcategories of sperm are excluded and not collected (resulting in high purity samples produced at slow sort rates and modest technical yields), a depletive sorting method is applied in which the highly selective output (i.e., live sperm having the undesired sex chromosome) is not collected, but rather discarded, while the remaining sperm are collected rather than sent to waste as in the selective sorting method.

In the context of selective sorting, the ratio of sort rate to event rate (i.e., technical yield) is inversely proportional to event rate (if all other sort gate settings remain the same), due to the increase in aborted drops at higher event rates. This creates a tradeoff between high sort rates (i.e., the number of desired cells removed from the total population per hour) and high technical yields (the percentage of cells from the total population recovered for use). When utilizing the high event rate, inverse sorting method of the invention, however, the tradeoff between high sort rate (in the context of depletive sorting, this is equivalent to the number of cells collected per hour after removal of undesired cells) and high technical yield, as seen with the sorting methods of the prior art, is significantly reduced.

Another aspect of the invention encompasses the use of enrich ("ENR") and purify ("PUR") sort modes. As noted above, in selective sorting, desired cells are identified, removed from the population, and collected for use, while the remaining population of cells is sent to waste. When using selective sorting, the ENR mode is particularly useful when the desired cells are rare (e.g., less than 5% of the total cell population). This is because the ENR mode disables the abort function, which would otherwise cause a drop containing both a desired and an undesired cell to be sent to waste. By allowing drops containing both a desired and an undesired cell to be removed from the cell population and collected for use, the ENR mode results in a higher number of desired cells being collected, at the cost of purity (i.e., the percentage of desired cells in the collected cell population). However, in the context of inverse sorting, the ENR mode actually results in higher purity levels, because when the abort function is disabled, drops containing both a desired cell and an undesired cell are removed from the cell population and sent to waste.

When using the PUR mode in selective sorting, a drop with a desired and an undesired cell is aborted—i.e., it is not removed and collected for use, but is instead sent to waste. This results in a higher percentage of desired cells in the collected population (i.e., higher purity). In inverse sorting, however, the PUR mode leaves the aborted cells in the collected stream, allowing undesired cells to remain in the collected sample. Because of this, in the context of inverse sorting, the PUR mode is significantly faster (more sperm collected per hour at higher technical yield) than the ENR mode, all else equal, but at the cost of purity.

In certain embodiments of the invention, both the selected and unselected streams may be collected and processed for breeding. For example, the invention can be performed in an "unbalanced" skew at ER/DDR rates higher than 0.85 in which a higher purity female sample (e.g., 70-90%) is collected for use in the stream containing the selected sperm, while the stream containing unselected sperm is collected for use as a lower purity male sample (e.g., 55-65%).

Some advantages of the invention include a significant reduction, in the number of sorters and in the time needed, to process an entire ejaculate, since the invention can analyze sperm at rates that are about 150-250% of the rate of prior art methods. Moreover, since the technical yield achieved by the invention is in the range of 60-75% (compared to technical yields of 25% or less with prior art methods), the invention is able to produce about 3-5 times more processed sperm per hour, while being about 2-3 times more efficient in sperm usage, compared to prior art methods. Additionally, because the invention uses the same amount of sheath fluid per hour as prior art methods (i.e., about 350 ml per hour), the amount of sheath fluid utilized per artificial insemination dose is reduced with the invention.

An additional advantage of the invention is that the number of breeding units (e.g., cryopreserved straws) from an ejaculate may be increased compared to conventional sperm. For example, if conventional sperm is typically used at a dose of about 25 million total sperm per breeding unit/straw and the same sperm can be processed by the invention with overall yields of 60% and formulated at a level of 8 million total sperm per breeding unit/straw, then about double the number of breeding units/straws may be produced from the same amount of ejaculate. For high value bulls where the number of ejaculates available across a period of time is not enough to serve the demand, then a process that produces such an increase in breeding units is highly desirable.

Another advantage of the invention is reduction in drop surface charge effect. Specifically, in prior art sex-sorting methods, each drop that is collected has an applied voltage differential pulsed in a way to charge the drop when it is still attached to the fluid stream and then reverse the polarity of the stream when the drop has broken from the stream. The charge pulse energy distributes mainly along the surface of the drop. Since the size of the drops are empirically determined by the smallest drop not causing a side stream effect, it is common that a small portion of the sperm tail, or even the leading edge of the sperm head may be at the surface of the drop or protrude from the drop when the charge pulse is applied. This charge pulse has a small but detrimental effect on the sperm quality. In contrast, when using the invention, the stream that is collected may have a slight but constant charge on it in order to control the angle of deflection, but the droplets leaving in that stream are not experiencing charge pulses.

One example of the method of the invention can be described as follows. One or more freshly ejaculated sperm samples is secured from the same bull and pooled into one sample. The pH and sperm cell concentration are stabilized and a portion of the seminal fluid is washed out. The sperm are stained with Hoechst 33342 (or another DNA-selective dye or stain). In a particular embodiment, the entire sperm sample is stained at one time and the sample quality confirmed on one sorter before choosing the operational conditions (parameter settings) for a group of sorters to sort the sperm. Another embodiment includes using magnetic particles to remove dead, dying or damaged cells in the stained sample, prior to re-concentration and sorting. The stained sperm are concentrated to high concentrations, for example, at concentrations in the range of 200 million-400 million stained sperm per ml. Alignment of the sperm sample is established while using an ER/DDR ratio of >0.85. Specific embodiments include the use of an ER/DDR ratio >0.85, in the range of 1.00-1.10, or >1.10. The stained sperm samples are sorted at high event rates (e.g., >40,000 events per second) and in some embodiments, with an ER/DDR ratio of about 1.00 with a high percentage of live-oriented cells (e.g., 80% or more of the total sperm population), while the undesired live sex are removed from the cell population by establishing an appropriate gate, typically comprising about 42-48% of the live-oriented population.

Flow cytometry data analysis and sorting are based on the principles of gating. Typically, gates are created around populations of cells with common characteristics. In the context of the invention, these characteristics can include forward fluorescence and side fluorescence. Generally, the first step in gating when flow cytometrically analyzing sperm is distinguishing populations of sperm based on their forward and side fluorescence properties. Forward and side fluorescence provide an estimate of the DNA content of the cells and their orientation, respectively. Unoriented sperm will generate events having a lower level of side fluorescence, as noted above, and generally are not resolvable or are low resolution. In some embodiments of the invention, these events can be removed by gating oriented sperm only. In other embodiments of the invention, these events are not removed, i.e., no gates are established. One aspect of the invention also comprises providing a gate on a multivariate plot encompassing a subpopulation of sperm—in certain embodiments of the invention, this subpopulation of sperm comprises undesired sperm and in other embodiments of the invention, this subpopulation of sperm comprises desired sperm; in a further embodiment, the subpopulation of sperm can further comprise dead, dying or damaged sperm.

Some embodiments of the invention comprise the use of event rates of >40,000 events per second ("eps"), 40,000-50,000 eps, 40,000-60,000 eps, 40,000-90,000 eps, >50,000 eps, 50,000-70,000 eps, >70,000 eps, or >100,000 eps. Additionally, in order to establish an ER/DDR ratio at >0.85 or higher, some embodiments of the invention comprise the use of a drop drive rate of >40,000 drop per second ("dps"), 40,000-50,000 dps, 40,000-60,000 dps, 40,000-90,000 dps, >50,000 dps, 50,000-70,000 dps, >70,000 dps, or >100,000 dps.

Certain embodiments include use of the ENR mode (which assures the most complete removal of the live cells having the undesired sex chromosome) and may include the gating of dead sperm for the purpose of removal. In one embodiment of the invention, the live-oriented sex gated sperm having the undesired sex chromosome are sorted into the selected stream location, while the unselected stream (i.e., all other cells) is collected for use into an appropriately sized fluid collection tube or container.

In certain embodiments of the invention sperm in the unselected stream are collected for use at a rate of >50,000 sperm per second, 30,000-50,000 sperm per second, 40,000-60,0000 sperm per second, 50,000-80,000 sperm per second, >60,000 sperm per second, >70,000 sperm per second or >80,000 sperm per second. Collected sperm may comprise both living and dead, dying or damaged sperm.

In one embodiment of the invention, diluted, collected sperm is concentrated using any appropriate method, such as centrifugation or membrane-based filtration, to provide a concentrated volume of sperm that may be subsequently processed for cryopreservation or used in appropriate fresh holding extenders for breeding within a short period.

The method of the invention requires the choice of an appropriate sheath fluid pressure. Certain embodiments of the invention comprise the use of 35-45 PSI sheath fluid pressure, but may include the use of pressures as high as 80 PSI, or higher. In specific embodiments, the invention encompasses, sheath fluid pressures of >35 PSI, >40 PSI, 35-40 PSI, 40-45 PSI, 40-50 PSI, 40-60 PSI, 40-80 PSI, 50-80 PSI, >50 PSI or 45-50 PSI.

At high sheath fluid pressures, the drop drive rate may be as high as 120,000 drops per second. Based on the chosen pressure, a drop drive frequency is then established empirically such that the last attached drop is placed at a correct distance from the nozzle tip. For calibration purposes, a concentrated stained sperm sample is placed on the sorter and a sample pressure is applied that is sufficient to create an ER/DDR ratio of 0.95-1.05 and a side stream quality calibration is made to determine appropriate drop drive amplitude and deflection voltage.

The appropriate concentrations of sperm cells and a DNA-selective dye (typically Hoechst 33342) are incubated in a staining media, at appropriate temperature, for appropriate time. Optimal conditions result in sperm cell populations that are evenly stained and not overstained, since overstaining is a problem that often leads to a poor peak to valley ratio (PVR) at high event rates.

In one embodiment of the invention, the concentration of sperm for staining is in the range of $50\text{-}150\times10^6$ sperm cells per ml, while the concentration of sperm in the sample tube that provides cells to the sorter may be in the range of $250\times10^6\text{-}400\times10^6$ cells per ml. In general, this difference leads to a required step to concentrate stained cells.

In one aspect of the invention, manual or automated fluidic and optical alignment settings are empirically applied to create and sustain the highest possible differentiation between live X-chromosome bearing and live Y-chromosome bearing sperm populations, while using event rates that come within the range of ER/DDR ratio between about 0.85 and 1.15, or higher. Careful attention to the quality of this differentiation, along with appropriate setting of live-oriented gates and sort gates for cell removal, is then provided to allow the depletive removal of sperm that have two primary characteristics: the first characteristic is that they are live sperm; the second characteristic is that they have a high statistical chance (e.g., greater than 85%) of having the undesired sex chromosome.

In one embodiment of the invention, as droplets containing undesired cells are removed, the gating logic may be chosen to apply the PUR mode or the ENR mode to analyzed droplets. When the PUR mode is applied, droplets are not removed into the selected stream location if a second or even third sperm is present with the targeted live cell having the undesired sex chromosome. In the inverse sorting method of the invention, since droplets containing desired cells are not removed and remain in the unselected stream (i.e., the collection stream) and undesired cells remains in the selected stream (the waste stream), the sex purity of the collected sperm subpopulation will be lower (less sex selected or enriched) when PUR mode is used. Conversely, when the ENR mode is used in the invention, droplets are always removed to the selected stream location when they contain an undesired cell, and as a result, the sex purity of the collected sperm subpopulation will be higher. As noted above, in the inverse sorting, high event rate method of the invention, the ENR mode generates a higher sex purity at the cost of a slower collection rate of desired cells.

In certain embodiments of the invention, the dead sperm are also selectively removed by the sorter. In this case, the target cells to be removed comprise two populations which may be gated separately but for which the same sort logic may be applied. It should be noted that in standard sperm sorting methods of the prior art, dead sperm are removed inherently because only live sperm are selected for collection. A region placed around the dead sperm is typically only used to quantify them and is not used as a sorting gate.

In certain embodiments of the inverse sorting, high event rate method of the invention, unless dead cells are also gated for removal with the sort gate, the dead cells will remain in the stream that is collected for use. Since dead cells are much less fertile than live cells (if fertile at all), retaining the dead cells in the collected stream should be neutral to breeding outcomes. Additionally, since the purity of undesired, live cells in the selected stream is high, the purity of the desired, live cells that are collected will be high, which should have a positive effect on breeding outcomes in terms of the percentage of offspring being of the desired sex for a given sperm cell sex purity.

As mentioned above, the inverse sorting high event rate method of the invention will generate a much larger fluid stream, nearly 400-600% greater, compared to standard flow cytometric sorting. Standard sorting typically utilizes catch, or collection, tubes holding 50 ml. Accordingly, one embodiment of the invention comprises sorting into a 500 ml, or larger, catch tube. One of the positive outcomes in using the inverse sorting, high event rate method of the invention in commercial scale is that the same number of sorters process about 150-250% the amount of raw ejaculate and produce about 4-6 times as much sperm per hour per sorter compared to prior art methods.

Since the inverse sorting, high even rate method of the invention benefits when sperm are stained at a lower concentration and then concentrated to double or triple the standard concentration, and since methods like treatment with magnetic particles for removal of dead, dying or damaged sperm may be somewhat more selective at lower sperm concentrations, one aspect of the invention encompasses a method for staining in large volumes (e.g., 150 ml, or more) at one time. In an additional embodiment of the invention, a multi-head flow cytometer for use in the invention utilizes a single laser for each sorting head, which results in an increase in the stability of the signal due to shorter laser path lengths.

Once obtained from a non-human mammal, sperm to be used with the invention may be standardized to a predetermined concentration and/or towards a predetermined pH. Each of the predetermined concentrations and pH may be specific to different species, or even to different breeds of animals within a species. In one embodiment, the sperm may be combined with an initial buffer in the form of a high capacity buffer. Exemplary buffers may include TRIS citrate, sodium citrate, sodium bicarbonate, HEPES, TRIS, TEST, MOPS, KMT, TALP, and combinations thereof. Any buffer having a high capacity for buffering pH may also be employed, and may be used in combination with additional components which promote sperm viability such as egg yolk, and sources of citrates or citric acid. Additionally, antioxidants and antibiotics may be employed in the initial buffer to promote sperm viability.

The initial buffer may be set at a predetermined pH to normalize the pH of all the obtained sperm samples. In one embodiment, the buffer is adjusted to a pH of 7.2. Additionally, semen may become increasingly acidic over time, possibly due to proteins in the seminal fluid, or due to acidic byproducts of dying or dead cells. The initial buffer introduces enough free proton (i.e., $H^+$) binding sites to maintain pH near the predetermined target. Even in light of the natural tendency for sperm to become more acidic over time, the initial buffer provides a means for stabilizing pH throughout additional processing steps.

As one example, the sperm sample may be diluted in the high capacity buffer in ratios from about 1:1 to about 1:10. The resulting mixture will have a sperm concentration many times below natural sperm concentrations for a particular species. The extended sperm may be centrifuged in order to reconcentrate sperm. Centrifuging the sperm and removing supernatant allows the sperm to be reconcentrated into a predetermined concentration. The predetermined concentration may be selected based on additional sperm processing steps. For example, in the case of sex sorting bovine sperm, sperm may be reconcentrated at between about 240 million sperm per ml and about 900 million sperm per ml to simulate a natural range of concentrations. Other concentrations, such as between about 1400 million sperm per ml and about 2100 million sperm per ml, or between about 1700 million sperm per ml and about 2100 million sperm per ml may also be achieved for further processing.

Adjusting the sperm concentration and pH may provide a uniform starting point for further processing. For example, a relatively consistent pH and concentration may provide greater predictability in staining sperm, for example with a DNA selective dye. If each sample is adjusted to the same predetermined pH and concentration, fewer trials may be required on each new collection to ensure adequate staining for sex sorting.

The population of sperm will include X-chromosome bearing sperm and Y-chromosome bearing sperm. Additionally, each of the X-chromosome bearing sperm and the Y-chromosome bearing sperm will include viable sperm and nonviable sperm. Viable sperm can be considered sperm with intact membranes while nonviable sperm can be considered sperm with compromised membranes. The distinction between viable sperm and non-viable sperm in conventional sperm sorting is determined with the inclusion of a quenching dye that permeates membrane compromised sperm. Sperm which tends to be dead or dying absorbs the quenching dye and produces fluorescence signals distinct from the remaining sperm population, whereas sperm cells having intact membranes tend to be viable sperm cells that will prevent uptake of the quenching dye. Viable sperm, in the appropriate dosage, will generally be capable of achieving fertilization using artificial insemination, while nonviable sperm, or membrane compromised sperm, may be incapable of achieving fertilization using artificial insemination or will have a greatly reduced ability to do so. However, some sperm capable of fertilization may have compromised membranes, and some sperm with intact membranes may be incapable of fertilization.

Whether standardized or not, sperm may be stained with a staining buffer for introducing a DNA-selective dye. In the staining step, at least a portion of the population of sperm is incubated with a staining buffer and a DNA-selective fluorescent dye in order to stoichiometrically stain the DNA content of each cell in the sperm population. Hoechst 33342 tends to be less toxic than other DNA selective dyes. The vehicle for delivering this dye may be in the form of a modified TALP buffer adjusted to a pH of about 7.4. Hoechst 33342 is described in U.S. Pat. No. 5,135,759 and is commonly used for this purpose. However, other UV excitable dyes, as well as visible light excitable dyes, fluorescent polyamides, fluorescent nucleotide sequences, and sex specific antibodies could also be used.

Sperm in a natural state is often not readily permeable to such dyes. In order to produce a uniform staining, the first step of staining can include incubating at least a portion of the sperm population at an elevated temperature in a staining buffer at an elevated pH in addition to the dye. Examples of appropriate first staining buffers can be a TALP, TES-TRIS, TRIS citrate, sodium citrate, or a HEPES based medium, each described in WO2005/095960, incorporated herein by reference. As one example, the population of sperm, or a portion of the population of sperm, could be diluted with a first buffer to between $640 \times 10^6$ and $40 \times 10^6$ sperm/ml, to between about $320 \times 10^6$ and $80 \times 10^6$ sperm/ml, or to about $160 \times 10^6$ sperm/ml in the first buffer. The DNA selective fluorescent dye can be added to the sperm suspended in the first buffer in a concentration of between about 10 μM and 200 μM; between about 20 μM and 100 or between about 30 μM and 70 μM. The pH of the first buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl.

While being stained, the population of sperm can be incubated between 30-39° C., between about 32-37° C., or at about 34° C. The period of incubation can range between about 20 minutes and about an hour and a half, between about 30 minutes and about 75 minutes, or for about 45 minutes to about 60 minutes. As one example, the population of sperm can be incubated for about 45 minutes at 34° C. In addition to the DNA-selective fluorescent dye, a quenching dye may be applied for the purpose of permeating membrane compromised sperm and quenching the signals they produce. A dead quenching dye can be understood to include dyes which differentially associate with membrane compromised sperm. It may be that these dyes enter membrane compromised sperm cells more easily because the membranes are breaking down or otherwise increasingly porous. It may also be that dead quenching dyes readily enter all sperm cells and that healthy sperm cells act to pump dead quenching dyes out faster than membrane compromised sperm. In either case, the sperm cells with which the dead quenching dyes associate includes a large portion of dead and dying sperm cells, although not necessarily all dead and dying sperm cells. The quenched signals produced from membrane compromised sperm having an association with quenching dye are distinct enough from the signals of healthy sperm that they may be removed from the further analysis and sorting applied to viable sperm.

In one embodiment, a second staining step is preformed which further reduces the concentration of sperm and introduces the dead quenching dye. The pH of the second staining solution may be targeted to achieve a target pH in the final sperm sample. Exemplary descriptions of two step staining processes are described in published PCT International Application WO 2011/123166 and International Application PCT/US12/58008, the entire disclosure of both are incorporated herein by reference.

In another embodiment, the quenching dye and the DNA selective dye are applied together in a single treatment. In this embodiment, the quenching dye is incubated along with the DNA selective dye at an elevated temperature in the modified TALP which may be at a pH of 7.4. In this embodiment, it is believed a synergy exists when the sperm is standardized at an elevated pH of about 7.2 before staining at 7.4. In this way, the pH to which the sperm is exposed remains in a constant range with minimal variations. Because both the staining buffer and the initial extender have high buffering capacities, it is believed the natural tendency of sperm to become more acidic over time will be avoided. Additionally, by minimizing the changes in pH seen by the sperm, it is believed the sperm are in a healthier condition to face the various pressures and stresses endured in the sex sorting process.

Sorting Stained Sperm

In one embodiment of the invention, sperm to be sorted are first processed by removing dead, dying or damaged sperm using magnetic particles, either before or after staining, as taught in WO 2014/035840 and WO 2016/090310, which are both incorporated by reference herein in their entirety.

In one aspect of the invention, it is contemplated that a sperm population is sorted by a flow cytometer. Referring to FIG. 1, a jet-in-air flow cytometer (10) is illustrated, although sorting may be performed with microfluidic chips or other types of flow cytometers, including flow cytometer having closed chambers and cytometers and cytometers incorporating ablating lasers. The flow cytometer (10) includes a cell source (12) for producing a flow of sperm sample, such as a flow of stained sperm sample, for sorting. The rate at which the sperm sample is delivered to the nozzle (14) may be considered the sample flow rate, and may be determined by a sample pressure applied at the cell source (12). The flow of stained sperm sample is deposited within a nozzle (14) and introduced into, or flowed into, a fluid stream (16) of sheath fluid (18). The sheath fluid (18) can be supplied by a sheath fluid source (20) so that as the cell source (12) supplies the sperm into the sheath fluid (18) they are concurrently fed through the nozzle (14). The sheath fluid (18) may be supplied at a sheath flow rate which is determined by a sheath pressure applied at the sheath fluid source (20). In this manner the sheath fluid (18) forms a fluid stream coaxially surrounding the sample having stained sperm which exits the nozzle (14) at the nozzle orifice (22). By providing an oscillator (24) which may be precisely controlled with an oscillator control (26), pressure waves may be established within the nozzle (14) and transmitted to the fluids exiting the nozzle (14) at nozzle orifice (22). In response to the pressure waves, the fluid stream (16) exiting the nozzle orifice (22) eventually forms regular droplets (28)

at precise intervals. The frequency, and to some extent the shape of the formed droplets may be controlled by a drop drive rate (i.e., frequency) and a drop drive amplitude supplied to the oscillator (24) or the oscillator controller (26).

Each droplet, so formed, retains the sheath fluid and sperm sample that previously formed a portion of the fluid stream (16). Because the stained sperm are surrounded by the fluid stream (16) or sheath fluid environment, the droplets (28) ideally contain individually isolated sperm. However, the sample concentration, sample pressure, and other instrument parameters dictate the frequency with which multiple cells will regularly occupy a single droplet, as well as the percentage of droplets containing sperm cells.

The flow cytometer (10) acts to sort droplets based on the characteristics of sperm predicted to be contained within the droplets. This can be accomplished through a cell sensing system (30) in communication with an analyzer (36). The cell sensing system (30) includes at least one sensor (32) responsive to the cells contained within fluid stream (16). The cell sensing system (30) provides data to the analyzer (36), which may cause an action depending upon the relative presence or relative absence of a characteristic of cells in the fluid stream (16). Certain characteristics, such as the relative DNA content of sperm cells, can be detected through excitation with a source of electromagnetic radiation (34), such as a laser generating an irradiation beam to which the stained sperm are responsive. The source of electromagnetic radiation (34) can be a laser operated at UV wavelength, such as at about 355 nm. An example of such a laser can be a Vanguard 350 (available from Spectra-Physics), which operates at 350 mW. Various optics may be employed to shape the beam profile of the laser, split the beam to more than one stream, or reduce the beam power at a stream. Non-limiting examples of such optics can be found in WO/2004/104178 and WO/2001/85913, each being incorporated herein by reference.

The characteristics of individual sperm, particularly the presence of an X-chromosome or a Y-chromosome can be determined from the detected fluorescence produced in response to the electromagnetic radiation source (34). In particular, configurations of the cell sensing system (30) may be in communication with an analyzer for providing a variety of fluorescence information, such as the forward fluorescence of an event, the side fluorescence of an event, or the amount of scatter associated with an event. The analyzer (36) may include written instructions for analyzing the signals produced by the one or more sensors (32) in the cell sensing system (30). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to identify, or differentiate between, X-bearing spermatozoa and Y-bearing spermatozoa, or to identify spermatozoa that are not X-bearing or spermatozoa that are not Y-bearing. Distinctions, such as sperm which is viable or not viable, may be differentiated in addition to oriented and unoriented sperm by the analyzer (36) according to sorting logic incorporated gating regions.

In order to achieve separation and isolation based upon stained sperm characteristics, emitted light can be detected by the sensor (32) and the information fed to an analyzer (36) coupled to a droplet charger that charges droplets (28) based upon the characteristics of the stained sperm contained within that droplet (28). In this manner the analyzer (36) acts to permit the electrostatic deflection plate (38) to deflect droplets (28) based on whether or not they contain the appropriate particle or cell. In one embodiment of the high event rate, inverse sorting method of the invention, the flow cytometer (10) removes sperm having the undesired sex chromosome from the population of sperm by diverting droplets containing sperm having the undesired sex chromosome (44) (i.e., the selected stream) to waste (40). The remaining droplets (i.e., the unselected stream) (46) are collected for use in a collection container (47) and constitute a subpopulation of sperm enriched for the desired sex.

A controller (42) may form a portion of the analyzer (36) or may be a component external to the analyzer (36). The illustrated controller (42) may also represent a collection of individual controllers. The controller (42) may receive signals or instructions from the analyzer (36) and in response may modify one or more instrument parameters, such as the sample flow rate, sample pressure, sheath flow rate, sheath pressure, drop drive rate, or drop drive amplitude and the like. The controller (42) may also provide an interface for operator input to manually adjust the sample flow rate, sample pressure, sheath flow rate, sheath pressure, drop drive frequency, drop drive amplitude and the like. The analyzer (36) may include written instructions for modifying the instrument parameters in response to measured sorting parameters, or modifications to instrument parameters may be manually performed by an operator adjusting various settings. The modifications to instrument parameters may be carried out in the analyzer (36) such as for changing sorting logic, abort logic, sorting regions, or gate regions and other parameters specific to making sort decisions in the analyzer (36). Additional modifications to instrument parameters may be effected by a controller (42), for controlling various external components to the analyzer, such as for controlling the sample pressure, sample flow rate, sheath pressure, sheath flow rate, drop drive rate, and drop drive amplitude.

Once collected, the subpopulation of sperm enriched for the desired sex can be further processed by, for example, cryopreserving the sperm, or packaging the sperm into doses for use in artificial insemination. In one embodiment of the invention, the collected subpopulation is also processed by removing dead, dying or damaged sperm using magnetic particles, as taught in WO 2016/090310, which is incorporated by reference herein in its entirety.

One aspect of the invention encompasses its use to produce sex sorted sperm samples for use in parent gilt multiplication in swine. The output in terms of parent gilts produced per sow per year is directly proportional to the level of sperm cell sorting. For instance, with the use of 65% X-chromosome bearing sperm cell samples instead of conventional semen, the output per sow per year can increase from 7.50 to 9.75 gilts/sow per year or, at a fixed output, the number of multiplication sows per 100 gilts can be reduced from 13.3 to 10.3.

Example 1

In this example, semen from two bulls was inverse sorted at four event rates-40,000 events per second ("eps"), 50,000 eps, 60,000 eps and 70,000 eps—using two different Y chromosome sort gates having removal levels of 35% and 55%, respectively. Each semen sample was collected in an extender. Sperm concentration was normalized to $1200 \times 10^6$ sperm/ml. The normalized sample was then stained at a concentration of $120 \times 10^6$ sperm/ml with Hoechst 33342 and applied to a flow cytometer for alignment at an event rate of 40,000 eps and calibration of drop delay. A sort gate for removal of Y chromosome sperm (i.e., the undesired sex chromosome in this case) was established in a population consisting of live-oriented sperm. ENR mode was enabled. The drop drive rate was 60,000 drops per second (i.e., 60 kHz). In order to determine the empirical abort rate, just prior to sorting at each experimental condition, the sperm were sorted in PUR mode, which shows the sort rate (i.e., rate of removal of undesired cells) and abort rate.

A standard catch tube with 3.5 ml of TRIS-based media was sorted to a final volume of 30 ml. Sperm were cooled for a minimum of 30 minutes and then centrifuged at 850 G for 20 min, the supernatant decanted and replaced with 2.0 ml of cold TRIS-based freezing media. These tubes were left overnight in the refrigerator. The following day, the volumes were determined gravimetrically, the sperm concentrations were measured by NucleoCounter (DF 11 as 1.0 ml S-100 and 100 µl sperm) to determine the millions sorted. 2 hours after sperm samples were removed from the refrigerator, the visual motilities (by microscope) and the CASA motilities (motility and progressive motility) of 2004, samples incubated for 15-30 minutes on a warm block were determined.

Two samples from the first bull were also sorted as "70Keps/50% GateDead" method. This is a method in which a sort gate for removal of both Y chromosome sperm and dead/damaged sperm was established form a gated population consisting of both live-oriented and dead/damaged sperm. This method was then tested in both the ENR and PUR modes. Processed samples were resorted to determine purity levels.

Results for this experiment are shown in Table 1 below. All samples were sex enriched to ranges greater than 55% and in the case of the 50% Y chromosome gate treatments, typically over 60%. With respect to Table 1, "Live-Oriented" represents the gated live-oriented cells as a percentage of the cell population of the sample; "Dead" represents the gated dead cells as a percentage of the cell population of the sample; "Remove Gate" represents the gated undesired cells removed from the gated live-oriented cells as a percentage of the gated live-oriented cells; "Purity" represents the collected undesired cells (both living and dead, dying or damaged) as a percentage of the collected cells (both living and dead, dying or damaged). For the samples examined by microscope, the last two samples (in which dead cells were selectively removed) received a quality rating of "4" on a scale of 1-5, while the other 16 samples scored as "3".

TABLE 1

| Bull | METHOD Event Rate and Remove Gate Percent | mode | Event Rate | Cell Harvest Rate | Cell Remove Rate | Live-Oriented | Dead | Remove Gate | Resort Purity | CASA MOT | CASA PROG |
|---|---|---|---|---|---|---|---|---|---|---|---|
| 1 | 40 KHz/35% | ENR | 40,758 | 31,430 | 9,328 | 77.4% | 9.5% | 35.9% | 58.0% | 89.2% | 73.1% |
| 1 | 40 KHz/50% | ENR | 39,745 | 25,939 | 13,806 | 77.5% | 10.1% | 55.0% | 62.2% | 82.1% | 67.5% |
| 1 | 50 KHz/35% | ENR | 49,541 | 38,576 | 10,965 | 75.3% | 10.7% | 37.1% | 58.8% | 86.3% | 70.5% |

TABLE 1-continued

| Bull | METHOD Event Rate and Remove Gate Percent | mode | Event Rate | Cell Harvest Rate | Cell Remove Rate | Live-Oriented | Dead | Remove Gate | Resort Purity | CASA MOT | CASA PROG |
|---|---|---|---|---|---|---|---|---|---|---|---|
| 1 | 50 KHz/50% | ENR | 49,212 | 33,486 | 15,726 | 75.2% | 11.0% | 55.0% | 62.1% | 79.1% | 64.7% |
| 1 | 60 KHz/35% | ENR | 59,265 | 48,173 | 11,092 | 72.0% | 11.3% | 34.9% | 58.5% | 85.2% | 69.1% |
| 1 | 60 KHz/50% | ENR | 59,756 | 42,459 | 17,297 | 71.5% | 11.8% | 56.1% | 59.7% | 85.2% | 70.0% |
| 1 | 70 KHz/35% | ENR | 68,137 | 58,250 | 9,887 | 66.5% | 14.6% | 35.5% | 55.0% | 66.1% | 47.4% |
| 1 | 70 KHz/50% | ENR | 60,553 | 46,983 | 13,570 | 61.5% | 15.2% | 52.8% | 57.0% | 84.3% | 66.6% |
| 2 | 40 KHz/35% | ENR | 41,190 | 31,832 | 9,358 | 78.1% | 8.9% | 35.3% | 58.5% | 87.6% | 55.0% |
| 2 | 40 KHz/50% | ENR | 39,631 | 25,406 | 14,225 | 78.7% | 8.7% | 55.3% | 63.9% | 91.8% | 62.5% |
| 2 | 50 KHz/35% | ENR | 49,267 | 39,230 | 10,037 | 76.0% | 8.7% | 36.5% | 57.3% | 90.5% | 51.4% |
| 2 | 50 KHz/50% | ENR | 49,780 | 33,540 | 16,240 | 75.7% | 8.7% | 55.6% | 59.7% | 89.5% | 59.8% |
| 2 | 60 KHz/35% | ENR | 60,261 | 48,109 | 12,152 | 72.8% | 8.9% | 37.0% | 57.0% | 62.2% | 44.1% |
| 2 | 60 KHz/50% | PUR | 59,531 | 46,503 | 13,028 | 72.8% | 8.9% | 55.5% | 56.8% | 89.5% | 61.5% |
| 2 | 70 KHz/35% | ENR | 69,153 | 56,926 | 12,227 | 70.7% | 9.3% | 38.0% | 55.4% | 87.2% | 52.8% |
| 2 | 70 KHz/50% | ENR | 66,354 | 54,667 | 11,687 | 68.6% | 10.0% | 54.6% | 54.5% | 68.8% | 46.7% |
| 1 | 70 KHz/50%/Gate with Dead | ENR | 71,440 | 39,106 | 32,334 | 90.7% | 14.1% | 58.7% | 60.6% | 88.8% | 71.2% |
| 1 | 70 KHz/50%/Gate with Dead | PUR | 69,980 | 47,904 | 22,076 | 90.7% | 14.8% | 57.9% | 57.4% | 84.5% | 70.2% |

Example 2

In this example, the range of event rates evaluated ranged from 50,000 eps to 90,000 eps, All samples, prior to being sorted, were processed as in Example 1. All samples were sorted with simultaneous dead removal (i.e., a sorting gate for both sperm having the undesired sex chromosome and dead/damaged sperm was established in a population consisting of live-oriented sperm and dead sperm), and both the ENR and PUR methods were compared. In total, almost 40 separate samples were sorted. Results are shown in Table 2 below and in FIGS. 2-9.

TABLE 2

| | Target Event Rate | Skew Direction | | ER/DDR | Method Name | Event Rate | Cell Harvest Rate |
|---|---|---|---|---|---|---|---|
| BULL 1 | 40 | X | ENR | 0.64 | 40K ENR REMY + DEAD | 38,552 | 14,297 |
| | 50K | X | ENR | 0.84 | 50K ENR REMY + DEAD | 50,557 | 20,013 |
| | | X | PUR | 0.82 | 50K PUR REMY + DEAD | 49,498 | 34,517 |
| | | Y | PUR | 0.84 | 50K PUR REMY + DEAD | 50,338 | 36,773 |
| | | Y | ENR | 0.88 | 50K ENR REMY + DEAD | 52,704 | 17,762 |
| | 60K | Y | ENR | 1.02 | 60K PUR REMY + DEAD | 61,322 | 25,310 |
| | | Y | PUR | 1.01 | 60K PUR REMY + DEAD | 60,660 | 50,330 |
| | | X | PUR | 0.97 | 60K PUR REMY + DEAD | 58,487 | 41,392 |
| | | X | ENR | 1.00 | 60K ENR REMY + DEAD | 59,904 | 17,577 |
| | 70K | X | ENR | 1.20 | 70K ENR REMY + DEAD | 71,721 | 26,378 |
| | | X | PUR | 1.18 | 70K PUR REMY + DEAD | 70,618 | 56,660 |
| | | Y | PUR | 1.20 | 70K PUR REMY + DEAD | 72,235 | 62,796 |
| | | Y | ENR | 1.19 | 70K ENR REMY + DEAD | 71,178 | 24,981 |
| | 80K | Y | ENR | 1.37 | 80K ENR REMY + DEAD | 82,259 | 31,479 |
| | | Y | PUR | 1.36 | 80K PUR REMY + DEAD | 81,677 | 70,319 |
| | | X | PUR | 1.36 | 80K PUR REMY + DEAD | 81,464 | 63,333 |
| | | X | ENR | 1.34 | 80K ENR REMY + DEAD | 80,170 | 21,954 |
| | 90K | Y | ENR | 1.48 | 90K ENR REMY + DEAD | 88,897 | 32,644 |
| | | Y | PUR | 1.50 | 90K PUR REMY + DEAD | 90,122 | 77,001 |
| BULL 2 | 50K | X | PUR | 0.87 | 50K PUR REMY + DEAD | 52,119 | 35,905 |
| | | X | ENR | 0.85 | 50K ENR REMY + DEAD | 50,777 | 16,427 |
| | | Y | ENR | 0.84 | 50K ENR REMX + DEAD | 50,356 | 19,010 |
| | | Y | PUR | 0.83 | 50K PUR REMX + DEAD | 49,800 | 38,872 |
| | 60K | Y | PUR | 1.04 | 60K PUR REMX + DEAD | 62,198 | 46,011 |
| | | Y | ENR | 1.04 | 60K ENR REMX + DEAD | 62,553 | 18,313 |
| | | X | ENR | 1.03 | 60K ENR REMY + DEAD | 61,865 | 16,389 |
| | | X | PUR | 1.04 | 60K PUR REMY + DEAD | 62,284 | 44,891 |
| | 70K | X | PUR | 1.21 | 70K PUR REMY + DEAD | 72,539 | 53,911 |
| | | X | ENR | 1.19 | 70K ENR REMY + DEAD | 71,659 | 16,508 |
| | | Y | ENR | 1.17 | 70K ENR REMX + DEAD | 70,319 | 21,800 |
| | | Y | PUR | 1.15 | 70K PUR REMX + DEAD | 69,070 | 53,371 |
| | 80K | Y | PUR | 1.33 | 80K PUR REMX + DEAD | 79,989 | 60,909 |
| | | Y | ENR | 1.32 | 80K ENR REMX + DEAD | 79,296 | 24,745 |
| | | X | ENR | 1.33 | 80K ENR REMY + DEAD | 79,862 | 31,434 |
| | | X | PUR | 1.36 | 80K PUR REMY + DEAD | 81,414 | 67,484 |
| | 90K | X | PUR | 1.51 | 90K PUR REMY + DEAD | 90,527 | 75,629 |
| | | X | ENR | 1.49 | 90K ENR REMY + DEAD | 89,696 | 27,636 |
| | | Y | ENR | 1.54 | 90K ENR REMX + DEAD | 92,143 | 29,658 |
| | | Y | PUR | 1.54 | 90K PUR REMX + DEAD | 92,320 | 73,438 |

TABLE 2-continued

| | Calculated Cell Remove Rate | Live-Oriented | Dead | Remove Gate | Live Sex Remove Gate | Resort Purity | CASA MOT | CASA PROG |
|---|---|---|---|---|---|---|---|---|
| BULL 1 | 24,255 | 93.0% | 8.8% | 58.1% | 49.3% | 68.6% | 88.3% | 68.3% |
| | 30,544 | 91.8% | 8.9% | 52.7% | 43.8% | 64.7% | 74.9% | 44.6% |
| | 14,981 | 91.8% | 9.1% | 54.0% | 44.9% | 58.5% | 88.5% | 52.6% |
| | 13,565 | 91.8% | 9.2% | 50.7% | 41.5% | 60.3% | 93.8% | 54.7% |
| | 34,942 | 91.6% | 9.2% | 49.8% | 40.7% | 65.6% | 91.2% | 72.0% |
| | 36,011 | 90.8% | 9.0% | 48.0% | 39.0% | 62.1% | 89.5% | 64.9% |
| | 10,330 | 90.9% | 8.9% | 47.8% | 38.9% | 55.4% | 69.5% | 36.8% |
| | 17,096 | 91.0% | 9.0% | 56.8% | 47.7% | 57.9% | 82.5% | 51.1% |
| | 42,327 | 90.9% | 9.0% | 55.1% | 46.1% | 62.3% | 75.4% | 49.2% |
| | 45,342 | 89.4% | 8.6% | 56.2% | 47.6% | 61.1% | 72.1% | 36.8% |
| | 13,958 | 89.6% | 8.6% | 55.0% | 46.4% | 52.7% | 83.4% | 53.4% |
| | 9,440 | 88.4% | 8.8% | 51.8% | 42.9% | 60.2% | 71.1% | 28.3% |
| | 46,197 | 89.5% | 9.0% | 45.8% | 36.8% | 63.0% | 78.4% | 55.8% |
| | 50,780 | 89.1% | 8.7% | 48.6% | 39.9% | 60.1% | 75.4% | 53.8% |
| | 11,358 | 89.0% | 8.7% | 50.1% | 41.4% | 55.8% | 66.4% | 41.5% |
| | 18,131 | 89.0% | 8.8% | 54.2% | 45.4% | 52.8% | 76.4% | 38.7% |
| | 58,216 | 89.1% | 8.7% | 54.8% | 46.0% | 56.0% | 69.5% | 45.6% |
| | 56,252 | 88.4% | 8.7% | 50.6% | 41.9% | 60.5% | 67.6% | 31.6% |
| | 13,121 | 88.3% | 8.7% | 52.3% | 43.6% | 55.5% | 62.3% | 38.7% |
| BULL 2 | 16,214 | 91.7% | 12.3% | 56.3% | 44.0% | 58.5% | 85.7% | 66.4% |
| | 34,350 | 91.7% | 12.2% | 57.5% | 45.2% | 63.9% | 91.1% | 74.3% |
| | 31,346 | 91.6% | 12.1% | 53.6% | 41.5% | 66.9% | 87.1% | 66.4% |
| | 10,928 | 91.7% | 12.1% | 55.9% | 43.8% | 61.7% | 75.4% | 59.9% |
| | 16,187 | 90.4% | 11.9% | 55.1% | 43.3% | 61.2% | 67.3% | 45.1% |
| | 44,240 | 90.2% | 11.7% | 53.1% | 41.4% | 63.9% | 82.5% | 46.9% |
| | 45,476 | 90.3% | 11.6% | 57.0% | 45.4% | 59.2% | 91.2% | 62.3% |
| | 17,393 | 90.3% | 11.6% | 57.8% | 46.2% | 58.9% | 84.8% | 44.2% |
| | 18,628 | 89.5% | 11.5% | 57.0% | 45.6% | 56.4% | 64.1% | 37.5% |
| | 55,151 | 89.4% | 11.6% | 60.9% | 49.3% | 61.1% | 92.1% | 71.5% |
| | 48,519 | 89.7% | 11.7% | 50.7% | 39.0% | 62.8% | 78.2% | 56.7% |
| | 15,699 | 89.7% | 11.9% | 52.4% | 40.5% | 58.8% | 80.0% | 63.0% |
| | 19,080 | 86.8% | 11.3% | 57.4% | 46.2% | 58.3% | 59.2% | 32.6% |
| | 54,551 | 87.0% | 11.3% | 57.0% | 45.7% | 58.9% | 88.1% | 67.2% |
| | 48,427 | 87.0% | 11.3% | 53.4% | 42.1% | 54.9% | 89.9% | 71.0% |
| | 13,930 | 86.9% | 11.2% | 56.0% | 44.7% | 54.0% | 71.1% | 46.2% |
| | 14,898 | 87.8% | 11.5% | 49.6% | 38.1% | 53.9% | 91.7% | 69.9% |
| | 62,059 | 87.8% | 11.5% | 50.8% | 39.3% | 57.1% | 75.8% | 54.9% |
| | 62,486 | 87.7% | 11.5% | 54.2% | 42.7% | 56.6% | 85.5% | 73.6% |
| | 18,882 | 87.5% | 11.2% | 55.6% | 44.4% | 54.1% | 87.4% | 71.9% |

Example 3

In this example, a higher sheath fluid pressure (60 PSI instead of the 40 PSI used in Examples 1 and 2) was used in order to increase the drop drive rate. In this way, event rates as high as 130,000 eps were evaluated. Prior to sorting, samples were processed as in Examples 1 and 2, above. Also in this example, inverse sorting was compared to selective, or standard, sorting as a control. Results are shown in Table 3 below.

TABLE 3

| Pressure (PSI) | DDR (KHz) | Method | | Event Rate | ER/DDR | Oriented | Y + Dead Gate | Dead | CALC Y Remove | Purity | CASA MOT |
|---|---|---|---|---|---|---|---|---|---|---|---|
| 60 | 90 | Standard X | ENR | 60 | 0.67 | 67.5% | 40.5% | 8.9% | | 85.7% | 59% |
| 60 | 90 | Standard X | PUR | 60 | 0.67 | 67.0% | 39.0% | 8.6% | | 87.9% | 76% |
| 60 | 90 | INV_REMY_DEAD | PUR | 60 | 0.67 | 68.0% | 42.0% | 8.0% | | 59.8% | 58% |
| 60 | 90 | INV_REMY_DEAD | PUR | 60 | 0.67 | 79.0% | 50.2% | 10.2% | 40.0% | 60.3% | 50% |
| 60 | 90 | INV_REMY_DEAD | ENR | 60 | 0.67 | 79.0% | 51.2% | 10.2% | 41.0% | 61.5% | 47% |
| 60 | 90 | INV_REMY_DEAD | ENR | 75 | 0.83 | 77.4% | 50.2% | 9.2% | 41.0% | 59.2% | 61% |
| 60 | 90 | INV_REMY_DEAD | PUR | 75 | 0.83 | 77.6% | 49.8% | 8.9% | 40.9% | 58.1% | 50% |
| 60 | 90 | INV_REMY_DEAD | PUR | 90 | 1.00 | 75.6% | 52.4% | 8.9% | 43.5% | 56.3% | 44% |
| 60 | 90 | INV_REMY_DEAD | ENR | 90 | 1.00 | 75.2% | 51.3% | 9.1% | 42.2% | 57.3% | 74% |
| 60 | 90 | INV_REMY_DEAD | ENR | 100 | 1.11 | 74.9% | 49.5% | 9.0% | 40.5% | 57.4% | 60% |
| 60 | 90 | INV_REMY_DEAD | PUR | 100 | 1.11 | 75.2% | 49.2% | 9.0% | 40.2% | 55.3% | 39% |
| 60 | 90 | INV_REMY_DEAD | PUR | 110 | 1.22 | 74.7% | 50.5% | 8.9% | 41.6% | 53.8% | 40% |
| 60 | 90 | INV_REMY_DEAD | ENR | 110 | 1.22 | 74.6% | 51.0% | 9.0% | 42.0% | 56.5% | 52% |
| 60 | 90 | INV_REMY_DEAD | ENR | 120 | 1.33 | 73.8% | 48.7% | 9.1% | 39.6% | 54.1% | 45% |
| 60 | 90 | INV_REMY_DEAD | PUR | 120 | 1.33 | 73.6% | 49.1% | 9.1% | 40.0% | 55.0% | 35% |
| 60 | 90 | INV_REMY_DEAD | PUR | 130 | 1.44 | 72.4% | 46.8% | 9.1% | 37.7% | 52.0% | 42% |
| 60 | 90 | INV_REMY_DEAD | ENR | 130 | 1.44 | 73.1% | 50.4% | 9.0% | 41.4% | 55.5% | 48% |

Example 4

In this Example, sperm from 5 bulls was processed as in Examples 1-3 above prior to sorting. Sorting was done at 40 PSI and an ER/DDR of 1.00 (60,000 eps/60,000 dps). Each bull's semen was sorted by two separate methods—by removing X-chromosome bearing sperm and by removing Y-chromosome bearing sperm—using the ENR mode and with removing dead cells with the sort gate, which gives the highest quality collected sperm at the cost of a lower collection rate. Collected sperm were cryopreserved and a post-thaw quality check was performed. The collection rate was determined empirically by using a NucleoCounter to determine the actual number of sperm that were collected (in the catch tube before centrifugation) and using the exact minutes and seconds that the sorting took (typically about 12-15 minutes to fill one catch tube). Results are shown in Tables 4A-9 below.

TABLE 4 A

|  |  | BULL 1 REMOVE X | SORT RATE | TOTAL | TIME (SEC) | TOTAL EVENTS |
|---|---|---|---|---|---|---|
| Aug. 23, 2016 | 12:49:17 | INV ENR REM_X_B1 | 9,234 | 33,348 |  |  |
| Aug. 23, 2016 | 12:49:27 | INV ENR REM_X_B1 | 9,095 | 322,683 | 10 | 622,508 |
| Aug. 23, 2016 | 12:49:58 | INV ENR REM_X_B1 | 30,930 | 1,304,503 | 32 | 2,051,086 |
| Aug. 23, 2016 | 12:51:58 | INV ENR REM_X_B1 | 30,941 | 5,013,976 | 120 | 7,795,988 |
| Aug. 23, 2016 | 12:53:59 | INV ENR REM_X_B1 | 30,751 | 8,699,179 | 120 | 7,796,751 |
| Aug. 23, 2016 | 12:55:59 | INV ENR REM_X_B1 | 30,183 | 12,364,291 | 120 | 7,793,317 |
| Aug. 23, 2016 | 12:57:59 | INV ENR REM_X_B1 | 30,322 | 16,018,085 | 120 | 7,818,392 |
| Aug. 23, 2016 | 12:59:59 | INV ENR REM_X_B1 | 30,319 | 19,652,260 | 120 | 7,815,215 |
| Aug. 23, 2016 | 13:01:59 | INV ENR REM_X_B1 | 29,940 | 23,256,030 | 120 | 7,802,708 |
| Aug. 23, 2016 | 13:03:59 | INV ENR REM_X_B1 | 29,869 | 26,855,473 | 120 | 7,807,911 |
| Aug. 23, 2016 | 13:05:46 | INV ENR REM_X_B1 | 29,959 | 30,077,357 | 106 | 6,922,602 |
| Aug. 23, 2016 | 13:05:46 | INV ENR REM_X_B1 | 29,957 | 30,099,583 | 1 | 56,633 |
| Aug. 23, 2016 | 13:05:58 | INV ENR REM_X_B1 | 24,142 | 30,232,956 | 11 | 732,498 |
|  |  |  |  | 30,232,956 | 1,001 | 65,015,609 |
|  |  |  |  |  | Y | 34,782,653 |
|  |  | PURITY | 54.8% |  |  | 28,000,000 |
|  | Straws Per Hour at 6Million | | 17 |  |  | 153,617,516 |
|  |  |  |  |  |  | 28,327 |
|  |  |  |  |  |  | 43% |

|  | TIME | LIVE-ORIENTED | DEAD | GATE | NET LIVE GATE |
|---|---|---|---|---|---|
| Aug. 23, 2016 |  | 86.4% | 10.6% | 66.17% | 55.59% |
| Aug. 23, 2016 |  | 86.4% | 10.6% | 66.48% | 55.85% |
| Aug. 23, 2016 |  | 86.3% | 10.7% | 67.89% | 57.20% |
| Aug. 23, 2016 |  | 86.3% | 10.6% | 66.89% | 56.25% |
| Aug. 23, 2016 |  | 86.4% | 10.8% | 66.87% | 56.06% |
| Aug. 23, 2016 |  | 86.4% | 10.8% | 66.29% | 55.53% |
| Aug. 23, 2016 |  | 86.4% | 10.8% | 65.88% | 55.13% |
| Aug. 23, 2016 |  | 86.4% | 10.8% | 65.68% | 54.84% |
| Aug. 23, 2016 |  | 86.5% | 10.9% | 65.49% | 54.58% |
| Aug. 23, 2016 |  | 86.4% | 10.9% | 65.45% | 54.55% |
| Aug. 23, 2016 |  | 86.4% | 10.9% | 65.28% | 54.36% |
| Aug. 23, 2016 |  | 86.3% | 10.9% | 65.26% | 54.35% |
| Aug. 23, 2016 |  | 86.4% | 10.9% | 65.00% | 54.09% |
|  | 0:16:28 | 86.4% | 10.8% | 66.0% | 55.3% |
|  |  | BEFORE ABORT LOSSES | | | |
|  | MEASURED RECOVERY/COLLECTED (NucleoCounter) | | | | |
|  | SPERM RECOVERED/COLLECTED PER HOUR | | | | |
|  | SPERM COLLECTED PER SECOND | | | | |
|  | TECHNICAL YIELD | | | | |

55

TABLE 4B

|  |  | BULL 1 REMOVE Y | SORT RATE | TOTAL | TIME (SEC) | TOTAL EVENTS |
|---|---|---|---|---|---|---|
| Aug. 23, 2016 | 13:32:13 | INV ENR REM_Y_B1 | 1,414 | 50,479 |  |  |
| Aug. 23, 2016 | 13:32:24 | INV ENR REM_Y_B1 | 13,585 | 359,295 | 11 | 695,805 |
| Aug. 23, 2016 | 13:32:24 | INV ENR REM_Y_B1 | 14,165 | 380,488 | 1 | 61,954 |
| Aug. 23, 2016 | 13:34:05 | INV ENR REM_Y_B1 | 29,336 | 3,331,547 | 100 | 6,643,276 |
| Aug. 23, 2016 | 13:36:05 | INV ENR REM_Y_B1 | 29,739 | 6,882,449 | 120 | 7,984,877 |
| Aug. 23, 2016 | 13:38:05 | INV ENR REM_Y_B1 | 29,753 | 10,438,405 | 120 | 7,966,300 |

TABLE 4B-continued

| | | | | | | |
|---|---|---|---|---|---|---|
| Aug. 23, 2016 | 13:40:05 | INV ENR REM_Y_B1 | 29,256 | 13,986,597 | 120 | 7,946,479 |
| Aug. 23, 2016 | 13:42:05 | INV ENR REM_Y_B1 | 30,231 | 17,560,336 | 120 | 7,975,278 |
| Aug. 23, 2016 | 13:44:05 | INV ENR REM_Y_B1 | 29,356 | 21,024,859 | 120 | 7,980,613 |
| Aug. 23, 2016 | 13:46:05 | INV ENR REM_Y_B1 | 29,306 | 24,540,335 | 120 | 7,970,236 |
| Aug. 23, 2016 | 13:46:40 | INV ENR REM_Y_B1 | 29,763 | 25,556,586 | 34 | 2,271,266 |
| Aug. 23, 2016 | 13:48:05 | INV ENR REM_Y_B1 | 29,179 | 28,101,301 | 86 | 5,688,772 |
| Aug. 23, 2016 | 13:50:06 | INV ENR REM_Y_B1 | 29,176 | 31,587,913 | 120 | 7,980,150 |
| Aug. 23, 2016 | 13:50:42 | INV ENR REM_Y_B1 | 28,672 | 32,631,075 | 37 | 2,403,387 |

| | | | |
|---|---|---|---|
| | | 32,631,075 | 1,109 | 73,568,394 |
| | | X | | 40,937,319 |
| PURITY | 56.0% | | | 25,000,000 |
| Stows Per Hour at 6M | 14 | | | 81,127,346 |
| | | | | 22,535 |
| | | | | 34% |

| | TIME | LIVE-ORIENTED | DEAD | GATE | NET LIVE GATE |
|---|---|---|---|---|---|
| Aug. 23, 2016 | | 86.2% | 11.6% | 63.67% | 52.06% |
| Aug. 23, 2016 | | 86.2% | 11.7% | 66.63% | 54.96% |
| Aug. 23, 2016 | | 86.2% | 11.7% | 66.75% | 55.08% |
| Aug. 23, 2016 | | 86.2% | 11.8% | 67.40% | 55.64% |
| Aug. 23, 2016 | | 86.3% | 11.8% | 67.08% | 55.26% |
| Aug. 23, 2016 | | 86.3% | 12.0% | 66.73% | 54.77% |
| Aug. 23, 2016 | | 86.3% | 12.0% | 66.41% | 54.41% |
| Aug. 23, 2016 | | 86.4% | 12.0% | 66.73% | 54.77% |
| Aug. 23, 2016 | | 86.4% | 12.1% | 66.26% | 54.19% |
| Aug. 23, 2016 | | 86.5% | 12.2% | 65.62% | 53.44% |
| Aug. 23, 2016 | | 86.5% | 12.2% | 65.76% | 53.56% |
| Aug. 23, 2016 | | 86.5% | 12.2% | 65.83% | 53.61% |
| Aug. 23, 2016 | | 86.7% | 12.5% | 64.93% | 52.43% |
| Aug. 23, 2016 | | 86.6% | 12.4% | 64.96% | 52.54% |
| | 0:18:29 | 86.4% | 12.0% | 66.1% | 54.1% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

35

TABLE 5A

| | BULL 2 REMOVE X | | SORT RATE | TOTAL | TIME (SEC) | TOTAL EVENTS |
|---|---|---|---|---|---|---|
| Aug. 23, 2016 | 14:16:08 | INV ENR REM_X_B2 | 0 | 13,113 | | |
| Aug. 23, 2016 | 14:17:13 | INV ENR REM_X_B2 | 4,748 | 136,648 | 65 | 4,133,714 |
| Aug. 23, 2016 | 14:17:14 | INV ENR REM_X_B2 | 6,008 | 173,384 | 1 | 90,255 |
| Aug. 23, 2016 | 14:18:08 | INV ENR REM_X_B2 | 23,786 | 1,477,625 | 54 | 3,448,938 |
| Aug. 23, 2016 | 14:20:08 | INV ENR REM_X_B2 | 24,636 | 4,408,074 | 120 | 7,661,980 |
| Aug. 23, 2016 | 14:22:06 | INV ENR REM_X_B2 | 24,553 | 7,279,458 | 118 | 7,526,447 |
| Aug. 23, 2016 | 14:22:09 | INV ENR REM_X_B2 | 24,550 | 7,332,938 | 3 | 165,218 |
| Aug. 23, 2016 | 14:24:09 | INV ENR REM_X_B2 | 25,422 | 10,272,795 | 120 | 7,667,785 |
| Aug. 23, 2016 | 14:26:09 | INV ENR REM_X_B2 | 24,264 | 13,182,808 | 120 | 7,669,411 |
| Aug. 23, 2016 | 14:27:24 | INV ENR REM_X_B2 | 24,504 | 14,998,815 | 75 | 4,791,927 |
| Aug. 23, 2016 | 14:27:24 | INV ENR REM_X_B2 | 24,514 | 15,017,010 | 0 | 28,490 |
| Aug. 23, 2016 | 14:27:28 | INV ENR REM_X_B2 | 23,729 | 15,071,575 | 4 | 222,235 |

| | | | |
|---|---|---|---|
| | | 15,071,575 | 680 | 43,406,401 |
| | | Y | | 28,334,826 |
| PURITY | 58.5% | | | 29,000,000 |
| Straws Per Hour at 6M | 26 | | | 153,617,516 |
| | | | | 42,672 |
| | | | | 67% |

| | TIME | LIVE-ORIENTED | DEAD | GATE | NET LIVE GATE |
|---|---|---|---|---|---|
| Aug. 23, 2016 | | 84.2% | 7.9% | 59.63% | 51.74% |
| Aug. 23, 2016 | | 84.2% | 7.9% | 60.75% | 52.87% |
| Aug. 23, 2016 | | 84.2% | 7.9% | 61.32% | 53.45% |
| Aug. 23, 2016 | | 84.2% | 7.8% | 60.71% | 52.91% |
| Aug. 23, 2016 | | 84.2% | 7.8% | 60.81% | 52.99% |
| Aug. 23, 2016 | | 84.1% | 7.9% | 61.08% | 53.22% |
| Aug. 23, 2016 | | 84.1% | 7.9% | 61.17% | 53.31% |
| Aug. 23, 2016 | | 84.1% | 7.8% | 61.40% | 53.58% |

TABLE 5A-continued

| | | | | | |
|---|---|---|---|---|---|
| Aug. 23, 2016 | | 84.1% | 7.8% | 61.40% | 53.59% |
| Aug. 23, 2016 | | 84.1% | 7.8% | 60.89% | 53.11% |
| Aug. 23, 2016 | | 84.1% | 7.8% | 60.90% | 53.12% |
| Aug. 23, 2016 | | 84.1% | 7.8% | 60.85% | 53.09% |
| | 0:11:20 | 84.1% | 7.8% | 60.9% | 53.1% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

TABLE 5B

| | | BULL 2 REMOVE Y | SORT RATE | TOTAL | TIME (SEC) | TOTAL EVENTS |
|---|---|---|---|---|---|---|
| Aug. 23, 2016 | 13:55:46 | INV ENR REM_Y_B2 | 31,905 | 1,248,222 | | |
| Aug. 23, 2016 | 13:56:07 | INV ENR REM_Y_B2 | 28,763 | 1,826,864 | 21 | 1,689,701 |
| Aug. 23, 2016 | 13:58:07 | INV ENR REM_Y_B2 | 25,440 | 4,853,557 | 120 | 7,723,781 |
| Aug. 23, 2016 | 14:00:07 | INV ENR REM_Y_B2 | 25,748 | 7,906,513 | 120 | 7,683,234 |
| Aug. 23, 2016 | 14:02:07 | INV ENR REM_Y_B2 | 24,189 | 10,891,344 | 120 | 7,653,956 |
| Aug. 23, 2016 | 14:04:07 | INV ENR REM_Y_B2 | 24,723 | 13,844,619 | 120 | 7,666,836 |
| Aug. 23, 2016 | 14:06:07 | INV ENR REM_Y_B2 | 24,517 | 16,816,796 | 120 | 7,653,310 |
| Aug. 23, 2016 | 14:07:01 | INV ENR REM_Y_B2 | 24,324 | 18,097,324 | 53 | 3,405,430 |
| Aug. 23, 2016 | 14:08:08 | INV ENR REM_Y_B2 | 25,251 | 19,779,849 | 67 | 4,268,095 |
| Aug. 23, 2016 | 14:10:08 | INV ENR REM_Y_B2 | 24,055 | 22,640,202 | 120 | 7,658,602 |
| Aug. 23, 2016 | 14:10:50 | INV ENR REM_Y_B2 | 24,954 | 23,674,031 | 42 | 2,672,546 |
| Aug. 23, 2016 | 14:11:42 | INV ENR REM_Y_B2 | 21,917 | 24,906,898 | 52 | 3,296,199 |
| | | | | 24,906,898 | 956 | 61,371,690 |
| | | | | X | | 36,464,792 |
| | | PURITY | 55.7% | | | 28,000,000 |
| | | Straws Per Hour at 6M | 18 | | | 105,422,348 |
| | | | | | | 29,284 |
| 8/23/2016 | | | | | | 46% |

| | | TIME | LIVE-ORIENTED | DEAD | GATE | NET LIVE GATE |
|---|---|---|---|---|---|---|
| | Aug. 23, 2016 | | 78.2% | 7.3% | 69.00% | 61.68% |
| | Aug. 23, 2016 | | 81.0% | 7.6% | 65.54% | 57.94% |
| | Aug. 23, 2016 | | 84.9% | 7.8% | 62.79% | 54.99% |
| | Aug. 23, 2016 | | 84.9% | 7.8% | 62.92% | 55.14% |
| | Aug. 23, 2016 | | 84.7% | 7.8% | 62.61% | 54.77% |
| | Aug. 23, 2016 | | 84.6% | 7.9% | 62.03% | 54.10% |
| | Aug. 23, 2016 | | 84.5% | 7.9% | 61.99% | 54.05% |
| | Aug. 23, 2016 | | 84.5% | 7.9% | 62.23% | 54.33% |
| | Aug. 23, 2016 | | 84.5% | 8.0% | 61.81% | 53.85% |
| | Aug. 23, 2016 | | 84.4% | 7.9% | 61.73% | 53.79% |
| | Aug. 23, 2016 | | 84.3% | 7.9% | 61.79% | 53.86% |
| | Aug. 23, 2016 | | 84.3% | 7.9% | 61.69% | 53.75% |
| | | 0:15:56 | 83.7% | 7.8% | 63.0% | 55.2% |
| | | | BEFORE ABORT LOSSES | | | |
| | | | MEASURED RECOVERY (NucleoCounter) | | | |
| | | | SPERM RECOVERED PER HOUR | | | |
| | | | EFFECTIVE SORT RATE BASED ON YIELD TO TRIS AB | | | |
| | 8/23/2016 | | TECHNICAL YIELD | | | |

TABLE 6A

| | | BULL 3 REMOVE X | SORT RATE | TOTAL | TIME (SEC) | TOTAL EVENTS |
|---|---|---|---|---|---|---|
| Aug. 24, 2016 | 16:39:22 | INV ENR REM_X_B3 | 0 | 0 | | |
| Aug. 24, 2016 | 16:40:13 | INV ENR REM_X_B3 | 2,781 | 83,376 | 51 | 3,131,266 |
| Aug. 24, 2016 | 16:40:15 | INV ENR REM_X_B3 | 4,883 | 134,829 | 2 | 144,587 |
| Aug. 24, 2016 | 16:41:23 | INV ENR REM_X_B3 | 21,993 | 1,645,372 | 67 | 4,206,886 |
| Aug. 24, 2016 | 16:43:23 | INV ENR REM_X_B3 | 22,656 | 4,373,575 | 120 | 7,424,917 |
| Aug. 24, 2016 | 16:45:23 | INV ENR REM_X_B3 | 25,949 | 7,424,528 | 120 | 7,447,735 |
| Aug. 24, 2016 | 16:47:23 | INV ENR REM_X_B3 | 25,132 | 10,510,062 | 120 | 7,436,269 |
| Aug. 24, 2016 | 16:49:09 | INV ENR REM_X_B3 | 25,230 | 13,232,647 | 106 | 6,546,857 |

TABLE 6A-continued

| | | | SORT RATE | TOTAL | TIME (SEC) | TOTAL EVENTS |
|---|---|---|---|---|---|---|
| Aug. 24, 2016 | 16:49:23 | INV ENR REM_X_B3 | 25,502 | 13,590,487 | 14 | 880,703 |
| Aug. 24, 2016 | 16:51:23 | INV ENR REM_X_B3 | 25,986 | 16,688,099 | 120 | 7,438,345 |
| Aug. 24, 2016 | 16:53:23 | INV ENR REM_X_B3 | 26,809 | 19,853,695 | 120 | 7,413,728 |
| Aug. 24, 2016 | 16:55:23 | INV ENR REM_X_B3 | 25,885 | 22,976,366 | 120 | 7,432,509 |
| Aug. 24, 2016 | 16:57:07 | INV ENR REM_X_B3 | 25,642 | 25,678,232 | 103 | 6,338,233 |
| | | | | 25,678,232 | 1,064 | 65,842,035 |
| | | | | Y | | 40,163,803 |
| | PURITY | | 59.3% | | | 42,000,000 |
| | Straws Per Hour at 6M | | 24 | | | 142,058,133 |
| | | | | | | 39,461 |
| | | | | | | 64% |

| | TIME | LIVE-ORIENTED | DEAD | GATE | NET LIVE GATE |
|---|---|---|---|---|---|
| Aug. 24, 2016 | | | | | |
| Aug. 24, 2016 | | 92.9% | 12.4% | 48.6% | 36.2% |
| Aug. 24, 2016 | | 92.9% | 12.4% | 49.1% | 36.7% |
| Aug. 24, 2016 | | 92.6% | 11.7% | 47.4% | 35.7% |
| Aug. 24, 2016 | | 92.6% | 11.7% | 48.6% | 37.0% |
| Aug. 24, 2016 | | 92.6% | 11.8% | 54.5% | 42.7% |
| Aug. 24, 2016 | | 92.7% | 11.8% | 54.6% | 42.8% |
| Aug. 24, 2016 | | 92.6% | 11.8% | 54.9% | 43.1% |
| Aug. 24, 2016 | | 92.7% | 11.8% | 54.7% | 42.9% |
| Aug. 24, 2016 | | 92.6% | 11.9% | 55.6% | 43.7% |
| Aug. 24, 2016 | | 92.6% | 12.1% | 56.8% | 44.6% |
| Aug. 24, 2016 | | 92.6% | 12.1% | 56.6% | 44.5% |
| Aug. 24, 2016 | | 92.6% | 12.1% | 56.6% | 44.5% |
| | 0:17:44 | 92.7% | 12.0% | 53.2% | 41.2% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

TABLE 6B

| | | BULL 3 REMOVE Y | SORT RATE | TOTAL | TIME (SEC) | TOTAL EVENTS |
|---|---|---|---|---|---|---|
| Aug. 24, 2016 | 16:57:10 | INV ENR REM_Y_B3 | 22,824 | 0 | | |
| Aug. 24, 2016 | 16:57:13 | INV ENR REM_Y_B3 | 19,465 | 0 | | |
| Aug. 24, 2016 | 16:57:23 | INV ENR REM_Y_B3 | 8,321 | 0 | | |
| Aug. 24, 2016 | 16:59:19 | INV ENR REM_Y_B3 | 27,311 | 1,894,150 | 115 | 7,119,484 |
| Aug. 24, 2016 | 16:59:19 | INV ENR REM_Y_B3 | 27,303 | 1,914,992 | 1 | 44,427 |
| Aug. 24, 2016 | 16:59:24 | INV ENR REM_Y_B3 | 27,362 | 2,038,416 | 4 | 264,836 |
| Aug. 24, 2016 | 17:01:24 | INV ENR REM_Y_B3 | 26,996 | 5,294,608 | 120 | 7,448,722 |
| Aug. 24, 2016 | 17:03:24 | INV ENR REM_Y_B3 | 26,752 | 8,515,192 | 120 | 7,415,335 |
| Aug. 24, 2016 | 17:05:24 | INV ENR REM_Y_B3 | 26,986 | 11,750,987 | 120 | 7,434,223 |
| Aug. 24, 2016 | 17:06:27 | INV ENR REM_Y_B3 | 27,068 | 13,453,882 | 63 | 3,899,936 |
| Aug. 24, 2016 | 17:06:29 | INV ENR REM_Y_B3 | 27,071 | 13,501,755 | 2 | 117,187 |
| Aug. 24, 2016 | 17:07:24 | INV ENR REM_Y_B3 | 27,077 | 14,995,123 | 55 | 3,419,487 |
| Aug. 24, 2016 | 17:09:25 | INV ENR REM_Y_B3 | 27,332 | 18,251,960 | 120 | 7,440,723 |
| Aug. 24, 2016 | 17:11:25 | INV ENR REM_Y_B3 | 26,841 | 21,477,082 | 120 | 7,432,032 |
| Aug. 24, 2016 | 17:13:25 | INV ENR REM_Y_B3 | 27,041 | 24,707,380 | 120 | 7,413,152 |
| Aug. 24, 2016 | 17:15:25 | INV ENR REM_Y_B3 | 0 | 27,080,060 | 120 | 7,433,550 |
| | | | | 27,080,060 | 1,082 | 59,763,610 |
| | | | | X | | 32,683,550 |
| | PURITY | | 52.2% | | | 42,000,000 |
| | Stows Per Hour at 6M | | 23 | | | 139,789,022 |
| | | | | | | 38,830 |
| | | | | | | 70% |

| | TIME | LIVE-ORIENTED | DEAD | GATE | NET LIVE GATE |
|---|---|---|---|---|---|
| Aug. 24, 2016 | | 92.6% | 12.1% | 56.5% | 44.4% |
| Aug. 24, 2016 | | 92.6% | 12.1% | 56.5% | 44.4% |
| Aug. 24, 2016 | | 92.7% | 12.1% | 56.2% | 44.2% |
| Aug. 24, 2016 | | 92.6% | 12.1% | 57.9% | 45.8% |
| Aug. 24, 2016 | | 92.6% | 12.1% | 57.9% | 45.8% |
| Aug. 24, 2016 | | 92.6% | 12.1% | 57.7% | 45.7% |
| Aug. 24, 2016 | | 92.6% | 12.2% | 55.8% | 43.7% |
| Aug. 24, 2016 | | 92.6% | 12.1% | 55.9% | 43.8% |

TABLE 6B-continued

| | | LIVE-ORIENTED | DEAD | GATE | NET LIVE GATE |
|---|---|---|---|---|---|
| Aug. 24, 2016 | | 92.6% | 12.1% | 56.3% | 44.2% |
| Aug. 24, 2016 | | 92.6% | 12.1% | 56.3% | 44.2% |
| Aug. 24, 2016 | | 92.6% | 12.1% | 56.3% | 44.2% |
| Aug. 24, 2016 | | 92.5% | 12.1% | 56.4% | 44.4% |
| Aug. 24, 2016 | | 92.5% | 12.1% | 56.5% | 44.4% |
| Aug. 24, 2016 | | 92.6% | 12.1% | 56.2% | 44.1% |
| Aug. 24, 2016 | | 92.6% | 12.1% | 55.9% | 43.9% |
| Aug. 24, 2016 | | 92.6% | 12.1% | 57.3% | 45.3% |
| | 0:18:02 | 92.6% | 12.1% | 56.6% | 44.6% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

15

TABLE 7A

| | | BULL 4 REMOVE X | SORT RATE | TOTAL | TIME (SEC) | TOTAL EVENTS |
|---|---|---|---|---|---|---|
| Aug. 24, 2016 | 15:25:59 | INV ENR REM_X_B4 | 0 | 0 | | |
| Aug. 24, 2016 | 15:26:11 | INV ENR REM_X_B4 | 4,340 | 121,136 | 12 | 697,168 |
| Aug. 24, 2016 | 15:27:17 | INV ENR REM_X_B4 | 26,328 | 1,855,021 | 67 | 3,961,499 |
| Aug. 24, 2016 | 15:29:17 | INV ENR REM_X_B4 | 24,757 | 4,819,574 | 120 | 7,087,139 |
| Aug. 24, 2016 | 15:31:18 | INV ENR REM_X_B4 | 24,417 | 7,846,790 | 120 | 7,135,810 |
| Aug. 24, 2016 | 15:33:18 | INV ENR REM_X_B4 | 25,341 | 10,848,011 | 120 | 7,155,376 |
| Aug. 24, 2016 | 15:35:18 | INV ENR REM_X_B4 | 24,517 | 13,807,468 | 120 | 7,186,757 |
| Aug. 24, 2016 | 15:36:29 | INV ENR REM_X_B4 | 24,628 | 15,524,507 | 71 | 4,205,028 |
| Aug. 24, 2016 | 15:37:18 | INV ENR REM_X_B4 | 24,781 | 16,741,755 | 49 | 2,926,996 |
| Aug. 24, 2016 | 15:39:18 | INV ENR REM_X_B4 | 23,640 | 18,899,870 | 120 | 7,149,588 |
| Aug. 24, 2016 | 15:41:18 | INV ENR REM_X_B4 | 23,962 | 21,737,803 | 120 | 7,133,491 |
| Aug. 24, 2016 | 15:42:16 | INV ENR REM_X_B4 | 23,199 | 23,076,144 | 57 | 3,395,105 |
| Aug. 24, 2016 | 15:42:18 | INV ENR REM_X_B4 | 22,424 | 23,111,417 | 2 | 143,680 |
| | | | | 23,111,417 | 979 | 58,177,639 |
| | | | | Y | | 35,066,222 |
| | | PURITY | 59.0% | | | 38,000,000 |
| | | Stows Per Hour at 6M | 23 | | | 139,703,457 |
| | | | | | | 38,807 |
| | | | | | | 65% |

| | TIME | LIVE-ORIENTED | DEAD | GATE | NET LIVE GATE |
|---|---|---|---|---|---|
| Aug. 24, 2016 | | | | | |
| Aug. 24, 2016 | | 92.6% | 16.6% | 58.1% | 41.5% |
| Aug. 24, 2016 | | 92.6% | 16.6% | 59.5% | 42.9% |
| Aug. 24, 2016 | | 92.7% | 16.6% | 53.5% | 36.9% |
| Aug. 24, 2016 | | 92.7% | 16.5% | 52.8% | 36.2% |
| Aug. 24, 2016 | | 92.7% | 16.6% | 52.9% | 36.3% |
| Aug. 24, 2016 | | 92.7% | 16.6% | 52.8% | 36.2% |
| Aug. 24, 2016 | | 92.7% | 16.6% | 52.8% | 36.2% |
| Aug. 24, 2016 | | 92.7% | 16.7% | 53.2% | 36.5% |
| Aug. 24, 2016 | | 92.7% | 16.7% | 50.9% | 34.2% |
| Aug. 24, 2016 | | 92.7% | 16.7% | 50.8% | 34.1% |
| Aug. 24, 2016 | | 92.7% | 16.7% | 50.8% | 34.1% |
| Aug. 24, 2016 | | 92.7% | 16.6% | 50.7% | 34.1% |
| | 0:16:19 | 92.7% | 16.6% | 53.6% | 37.0% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

TABLE 7B

| | | BULL 4 REMOVE Y | SORT RATE | TOTAL | TIME (SEC) | TOTAL EVENTS |
|---|---|---|---|---|---|---|
| Aug. 24, 2016 | 15:43:19 | INV ENR REM_Y_B4 | 0 | 0 | | |
| Aug. 24, 2016 | 15:44:30 | INV ENR REM_Y_B4 | 2,699 | 79,162 | 71.52 | 4,201,390 |

TABLE 7B-continued

| Aug. 24, 2016 | 15:45:19 | INV ENR REM_Y_B4 | 26,550 | 1,376,872 | 49 | 3,007,303 |
|---|---|---|---|---|---|---|
| Aug. 24, 2016 | 15:47:19 | INV ENR REM_Y_B4 | 27,840 | 4,666,947 | 120 | 7,375,455 |
| Aug. 24, 2016 | 15:49:19 | INV ENR REM_Y_B4 | 25,853 | 7,873,046 | 120 | 7,372,456 |
| Aug. 24, 2016 | 15:49:20 | INV ENR REM_Y_B4 | 25,881 | 7,911,820 | 1 | 89,901 |
| Aug. 24, 2016 | 15:51:19 | INV ENR REM_Y_B4 | 27,698 | 11,057,298 | 119 | 7,317,938 |
| Aug. 24, 2016 | 15:53:19 | INV ENR REM_Y_B4 | 27,236 | 14,273,385 | 120 | 7,400,047 |
| Aug. 24, 2016 | 15:55:19 | INV ENR REM_Y_B4 | 26,495 | 17,477,322 | 120 | 7,383,017 |
| Aug. 24, 2016 | 15:57:19 | INV ENR REM_Y_B4 | 26,696 | 20,730,544 | 120 | 7,380,124 |
| Aug. 24, 2016 | 15:59:20 | INV ENR REM_Y_B4 | 27,104 | 24,014,725 | 120 | 7,389,357 |
| Aug. 24, 2016 | 16:01:09 | INV ENR REM_Y_B4 | 26,607 | 26,954,167 | 109 | 6,697,674 |
| Aug. 24, 2016 | 16:01:12 | INV ENR REM_Y_B4 | 25,633 | 27,012,489 | 3 | 202,694 |
| | | | | 27,012,489 | 1,073 | 65,817,356 |
| | | | | X | | 38,804,867 |
| | PURITY | | 56.2% | | | 42,000,000 |
| | Stews Per Hour at 6M | | 23 | | | 140,881,291 |
| | | | | | | 39,134 |
| | | | | | | 64% |

| | TIME | LIVE-ORIENTED | DEAD | GATE | NET LIVE GATE |
|---|---|---|---|---|---|
| Aug. 24, 2016 | | | | | |
| Aug. 24, 2016 | | 92.8% | 16.6% | 59.0% | 42.4% |
| Aug. 24, 2016 | | 92.6% | 16.5% | 57.1% | 40.5% |
| Aug. 24, 2016 | | 92.6% | 16.6% | 56.7% | 40.1% |
| Aug. 24, 2016 | | 92.6% | 16.6% | 56.9% | 40.3% |
| Aug. 24, 2016 | | 92.6% | 16.6% | 57.0% | 40.4% |
| Aug. 24, 2016 | | 92.6% | 16.6% | 57.2% | 40.6% |
| Aug. 24, 2016 | | 92.7% | 16.6% | 57.1% | 40.5% |
| Aug. 24, 2016 | | 92.6% | 16.7% | 56.7% | 40.1% |
| Aug. 24, 2016 | | 92.6% | 16.6% | 57.2% | 40.6% |
| Aug. 24, 2016 | | 92.6% | 16.6% | 57.0% | 40.3% |
| Aug. 24, 2016 | | 92.6% | 16.6% | 57.3% | 40.7% |
| Aug. 24, 2016 | | 92.6% | 16.6% | 57.3% | 40.7% |
| | 0:17:53 | 92.6% | 16.6% | 57.0% | 40.4% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

TABLE 8A

| | | BULL 5 REMOVE X | SORT RATE | TOTAL | TIME (SEC) | TOTAL EVENTS |
|---|---|---|---|---|---|---|
| Aug. 24, 2016 | 16:23:21 | INV ENR REM_X_B5 | 10,412 | 274,257 | 120 | 7,139,663 |
| Aug. 24, 2016 | 16:23:24 | INV ENR REM_X_B5 | 12,991 | 337,062 | 3 | 170,379 |
| Aug. 24, 2016 | 16:23:26 | INV ENR REM_X_B5 | 14,939 | 392,820 | 2 | 142,943 |
| Aug. 24, 2016 | 16:25:21 | INV ENR REM_X_B5 | 20,136 | 2,766,174 | 115 | 6,951,908 |
| Aug. 24, 2016 | 16:27:22 | INV ENR REM_X_B5 | 20,330 | 5,211,250 | 120 | 7,227,246 |
| Aug. 24, 2016 | 16:29:22 | INV ENR REM_X_B5 | 20,763 | 7,701,630 | 120 | 7,220,736 |
| Aug. 24, 2016 | 16:31:22 | INV ENR REM_X_B5 | 21,170 | 10,189,443 | 120 | 7,233,042 |
| Aug. 24, 2016 | 16:33:22 | INV ENR REM_X_B5 | 20,969 | 12,716,527 | 120 | 7,228,917 |
| Aug. 24, 2016 | 16:35:22 | INV ENR REM_X_B5 | 20,806 | 15,202,349 | 120 | 7,230,294 |
| Aug. 24, 2016 | 16:37:22 | INV ENR REM_X_B5 | 20,795 | 17,697,093 | 120 | 7,221,184 |
| Aug. 24, 2016 | 16:38:05 | INV ENR REM_X_B5 | 21,145 | 18,623,045 | 43 | 2,603,267 |
| Aug. 24, 2016 | 16:38:09 | INV ENR REM_X_B5 | 19,967 | 18,662,040 | 3 | 200,665 |
| Aug. 24, 2016 | 16:38:10 | INV ENR REM_X_B5 | 19,543 | 18,662,040 | 1 | 58,268 |
| | | | | 18,662,040 | 1,009 | 53,318,469 |
| | | | | Y | | 34,656,429 |
| | PURITY | | 58.8% | | | 43,000,000 |
| | Stews Per Hour at 6M | | 26 | | | 153,449,643 |
| | | | | | | 42,625 |
| | | | | | | 81% |

| | TIME | LIVE-ORIENTED | DEAD | GATE | NET LIVE GATE |
|---|---|---|---|---|---|
| Aug. 24, 2016 | | 90.8% | 5.7% | 46.5% | 40.7% |
| Aug. 24, 2016 | | 90.8% | 5.7% | 46.9% | 41.2% |
| Aug. 24, 2016 | | 90.8% | 5.7% | 47.2% | 41.5% |
| Aug. 24, 2016 | | 90.6% | 5.6% | 47.2% | 41.6% |
| Aug. 24, 2016 | | 90.7% | 5.6% | 47.3% | 41.7% |

TABLE 8A-continued

| | | | | | |
|---|---|---|---|---|---|
| Aug. 24, 2016 | | 90.8% | 5.6% | 47.4% | 41.8% |
| Aug. 24, 2016 | | 90.8% | 5.6% | 47.6% | 42.0% |
| Aug. 24, 2016 | | 90.8% | 5.6% | 47.5% | 41.9% |
| Aug. 24, 2016 | | 90.9% | 5.7% | 48.0% | 42.3% |
| Aug. 24, 2016 | | 90.9% | 5.6% | 48.0% | 42.4% |
| Aug. 24, 2016 | | 90.9% | 5.6% | 47.7% | 42.1% |
| Aug. 24, 2016 | | 90.9% | 5.6% | 47.7% | 42.1% |
| Aug. 24, 2016 | | 90.9% | 5.6% | 47.7% | 42.0% |
| | 0:16:49 | 90.8% | 5.6% | 47.4% | 41.8% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

15

TABLE 8B

| | | BULL 5 REMOVE Y | SORT RATE | TOTAL | TIME (SEC) | TOTAL EVENTS |
|---|---|---|---|---|---|---|
| Aug. 24, 2016 | 16:03:20 | INV ENR REM_Y_B5 | 0 | 0 | | |
| Aug. 24, 2016 | 16:05:00 | INV ENR REM_Y_B5 | 1,521 | 45,322 | 101 | 6,158,478 |
| Aug. 24, 2016 | 16:05:04 | INV ENR REM_Y_B5 | 4,987 | 145,509 | 4 | 233,083 |
| Aug. 24, 2016 | 16:05:20 | INV ENR REM_Y_B5 | 18,544 | 525,158 | 16 | 950,835 |
| Aug. 24, 2016 | 16:07:20 | INV ENR REM_Y_B5 | 19,699 | 3,378,417 | 120 | 7,270,439 |
| Aug. 24, 2016 | 16:09:20 | INV ENR REM_Y_B5 | 22,254 | 5,472,451 | 120 | 7,217,618 |
| Aug. 24, 2016 | 16:11:20 | INV ENR REM_Y_B5 | 22,449 | 8,164,448 | 120 | 7,199,972 |
| Aug. 24, 2016 | 16:13:20 | INV ENR REM_Y_B5 | 22,074 | 10,837,026 | 120 | 7,192,848 |
| Aug. 24, 2016 | 16:15:21 | INV ENR REM_Y_B5 | 21,593 | 13,478,622 | 120 | 7,229,656 |
| Aug. 24, 2016 | 16:17:21 | INV ENR REM_Y_B5 | 21,845 | 16,171,610 | 120 | 7,226,619 |
| Aug. 24, 2016 | 16:19:21 | INV ENR REM_Y_B5 | 22,452 | 18,840,137 | 120 | 7,222,437 |
| Aug. 24, 2016 | 16:20:53 | INV ENR REM_Y_B5 | 20,858 | 20,820,523 | 92 | 5,470,771 |
| | | | | 20,820,523 | 1,053 | 63,372,757 |
| | | | | X | | 42,552,234 |
| | | PURITY | 59.0% | | | 45,000,000 |
| | | Straws Per Hour at 6M | 26 | | | 153,798,539 |
| | | | | | | 42,722 |
| | | | | | | 71% |

| | TIME | LIVE-ORIENTED | DEAD | GATE | NET LIVE GATE |
|---|---|---|---|---|---|
| Aug. 24, 2016 | | | | | |
| Aug. 24, 2016 | | 91.3% | 5.5% | 57.6% | 52.1% |
| Aug. 24, 2016 | | 91.2% | 5.4% | 56.7% | 51.3% |
| Aug. 24, 2016 | | 91.3% | 5.5% | 54.8% | 49.3% |
| Aug. 24, 2016 | | 91.4% | 5.5% | 53.6% | 48.1% |
| Aug. 24, 2016 | | 91.4% | 5.6% | 49.7% | 44.1% |
| Aug. 24, 2016 | | 91.3% | 5.6% | 49.2% | 43.6% |
| Aug. 24, 2016 | | 91.3% | 5.6% | 49.0% | 43.3% |
| Aug. 24, 2016 | | 91.2% | 5.7% | 48.8% | 43.1% |
| Aug. 24, 2016 | | 91.2% | 5.7% | 49.1% | 43.5% |
| Aug. 24, 2016 | | 91.0% | 5.6% | 49.4% | 43.8% |
| Aug. 24, 2016 | | 91.0% | 5.7% | 49.1% | 43.5% |
| | 0:17:33 | 91.2% | 5.6% | 51.5% | 46.0% |

BEFORE ABORT LOSSES
MEASURED RECOVERY (NucleoCounter)
SPERM RECOVERED PER HOUR
EFFECTIVE SORT RATE BASED ON YIELD TO TRIS AB
TECHNICAL YIELD

TABLE 9

| | | PUR-ITY | 0-HOUR VISUAL MOTILITY | 3-HOUR VISUAL MOTILITY | RATIO 3 H/0 H |
|---|---|---|---|---|---|
| BULL 1 | Remove X | 54.8% | 57.0% | 45.0% | 78.9% |
| | Remove Y | 56.0% | 58.0% | 57.0% | 98.3% |
| BULL 2 | Remove X | 58.5% | 58.0% | 36.0% | 62.1% |
| | Remove Y | 55.7% | 55.0% | 48.0% | 87.3% |
| BULL 3 | Remove X | 59.3% | 54.0% | 39.0% | 72.2% |
| | Remove Y | 52.2% | 55.0% | 34.0% | 61.8% |
| BULL 4 | Remove X | 59.0% | 48.0% | 42.0% | 87.5% |
| | Remove Y | 56.2% | 49.0% | 50.0% | 102.0% |
| BULL 5 | Remove X | 58.8% | 68.0% | 41.0% | 60.3% |
| | Remove Y | 59.0% | 60.0% | 48.0% | 80.0% |
| AVERAGE | Remove X | 58.1% | 57.0% | 40.6% | 71.2% |
| | Remove Y | 55.8% | 55.4% | 47.4% | 85.6% |

Example 5

1. Get three fresh ejaculates each from a different bull.
2. Check volume, concentration, motility, morphology and pH. Add antibiotics.

12. Bulk sort (standard) sperm into 7.0 mL of Tris based media to a final of 40 mL with sheath fluid (6 pre-weighted tubes total).

13. Using the Y gate, remove a percentage of sperm that is close to the dead percentage plus 45%.

14. Inverse sort sperm into 7.0 mL of Tris based media to a final of 40 ml with sheath fluid (6 pre-weighted tubes total).

15. Place all catch tubes in a CoolingCastle at the same time and for a minimum of 30 minutes.

16. Centrifuge all tubes and decant following production procedures. Calculate recovery (using tare and end weight of tubes and final concentration of pellets).

17. Add freezing media for a final of 6 million sperm per ¼ cc straw.

18. Hold sperm over-night in freezing media and freeze (3 straws per treatment).

19. Perform quality control check for 0 and 3 h motility, viability (PI) and PIA (PNA). Perform purity analysis.

Figure 10:
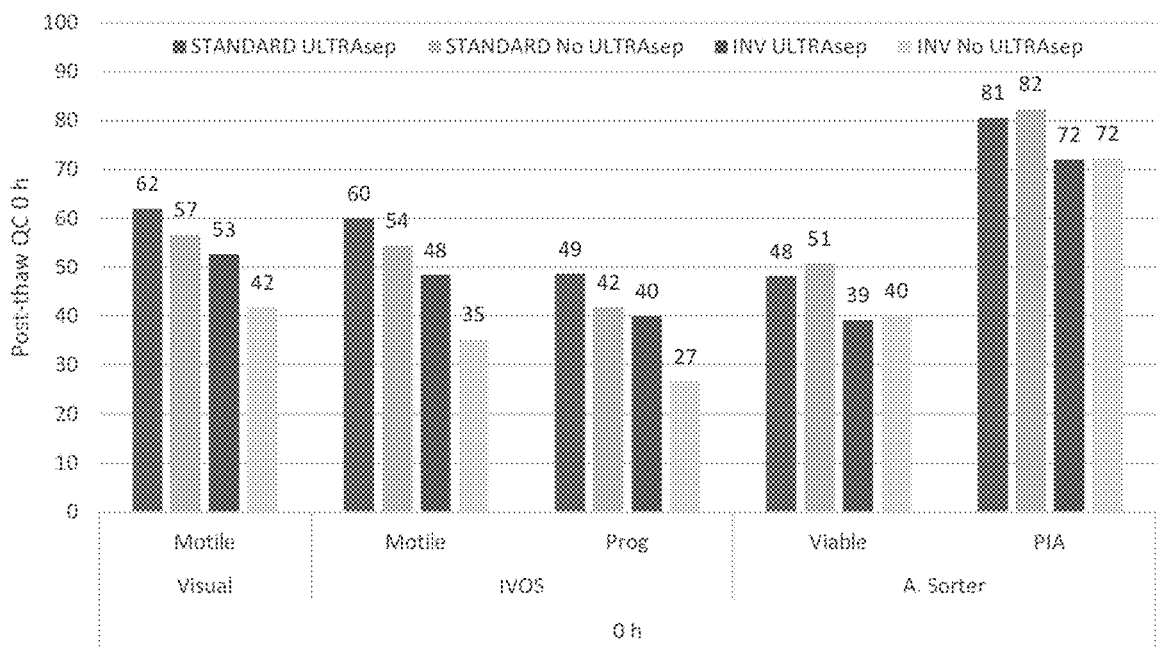
FIG. 10 is a graph showing post-thaw 0-hour motility, viability and percent intact acrosomes of collected sperm achieved with the invention with and without treatment with magnetic particles.
Figure 11:
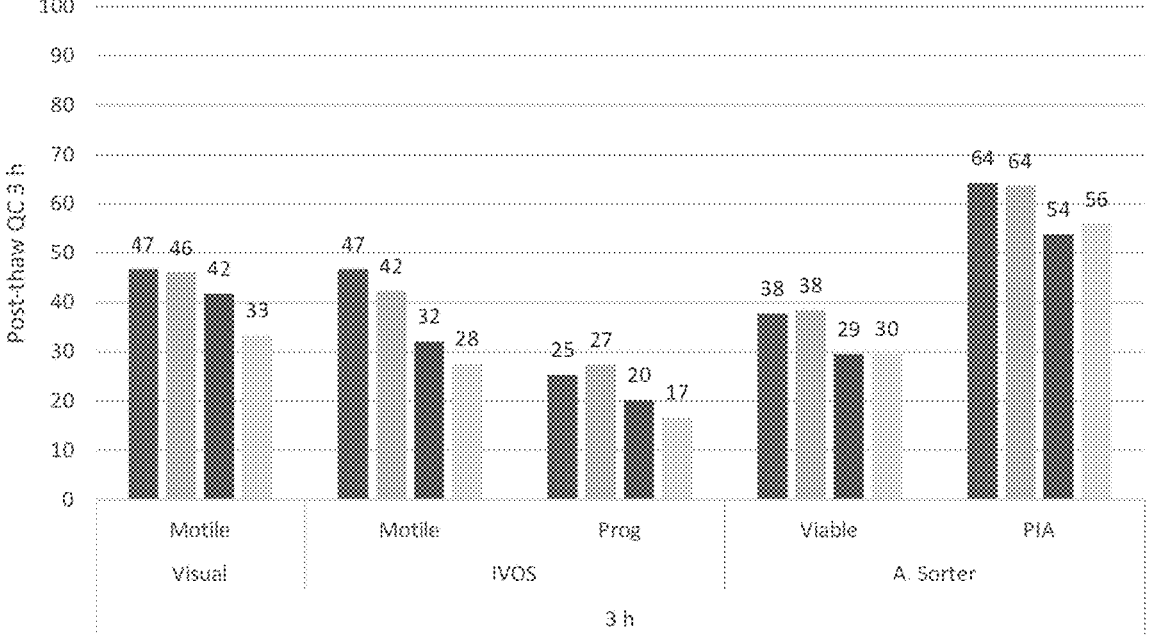
FIG. 11 is a graph showing post-thaw 3-hour motility, viability and percent intact acrosomes of collected sperm achieved with the invention with and without treatment with magnetic particles.

Results of the experiment are found in Table 10 below and in FIGS. 10 and 11.

TABLE 10

| Bull | Method | Sorted Time | EVENT AVG | SORT AVG | TOTAL SORT | ORI-ENTED AVG | DEAD AVG | X AVG | PVR AVG | NET Gate | MILLION RECOVERED (1TUBE) | MILLION SORTED/ MIN | PURI-TY |
|---|---|---|---|---|---|---|---|---|---|---|---|---|---|
| B1 | PVR Check | | 50,404 | | | | | | 61.7% | | | | |
| | Standard | 0:29:02 | 50,224 | 20,698 | 37,010,494 | 64.8% | 11.0% | 99.3% | 58.6% | | 41.9 | 1.4 | 50.0% |
| | | 0:27:10 | 49,909 | 22,579 | 38,038,888 | 69.1% | 9.7% | 99.3% | 55.8% | | 44.7 | 1.7 | 50.0% |
| | Inverse | 0:12:17 | 65,093 | 38,626 | 28,448,852 | 88.4% | 11.4% | 60.2% | 22.4% | 48.8% | 32.5 | 2.7 | 60.4% |
| | | 0:11:18 | 64,825 | 40,006 | 27,134,067 | 87.3% | 9.5% | 57.5% | 14.6% | 48.0% | 36.6 | 3.3 | 60.5% |
| | PVR Check | | 79,838 | | | | | | 52.6% | | | | |
| B2 | PVR Check | | 51,818 | | | | | | 64.9% | | | | |
| | Standard | 0:24:27 | 50,836 | 25,239 | 38,355,238 | 74.2% | 7.6% | 99.1% | 65.3% | | 45.1 | 1.9 | 50.0% |
| | | 0:24:34 | 50,429 | 25,105 | 37,994,720 | 73.8% | 7.9% | 99.2% | 63.6% | | 42.6 | 1.8 | 50.0% |
| | Inverse | 0:11:47 | 65,193 | 41,791 | 29,526,163 | 87.8% | 7.5% | 57.3% | 45.1% | 49.9% | 33.5 | 2.8 | 58.5% |
| | | 0:11:57 | 65,218 | 39,117 | 28,050,183 | 87.4% | 7.4% | 60.9% | 43.4% | 53.5% | 33.6 | 2.8 | 60.9% |
| | PVR Check | | 87,310 | | | | | | 55.8% | | | | |
| B3 | PVR Check | | 51,448 | | | | | | 54.7% | | | | |
| | Standard | 0:25:25 | 50,788 | 23,998 | 37,693,153 | 70.6% | 10.4% | 99.1% | 53.0% | | 45.6 | 1.8 | 50.0% |
| | | 0:26:03 | 50,537 | 23,008 | 36,993,115 | 69.8% | 11.0% | 98.0% | 52.6% | | 39.7 | 1.5 | 50.0% |
| | Inverse | 0:10:31 | 65,100 | 47,101 | 29,729,475 | 88.7% | 9.7% | 61.2% | 1.8% | 51.4% | 37.6 | 3.8 | 41.2% |
| | | 0:10:42 | 65,590 | 49,550 | 31,817,520 | 88.4% | 10.9% | 57.4% | 1.3% | 46.4% | 36.1 | 3.6 | 42.9% |
| | PVR Check | | 80,560 | | | | | | 45.7% | | | | |

3. Standardize with an extender, concentrate to 1800 mill/ml.
4. Stain 20 mL sperm per tube at 160 million sperm per mL with Hoechst 33342.
5. Once the staining mix is created, split the volume in two aliquots (10 mL each):
   Add magnetic particles (ULTRAsep) to ALIQUOT A.
   No ULTRAsep will be added to ALIQUOT B.
6. Incubate for 60 minutes at 34° C. and apply the separation system for 10 minutes to the ULTRAsep treated sample.
7. Add ⅓ vol of 8% egg yolk TALP-based media to each aliquot.
8. Transfer to 15 mL Falcon tubes, centrifuge and remove an amount of supernatant to target a new concentration of 320 sperm/ml.
9. Confirm the final concentrations and place the fluid volumes into 6 mL tubes for use on Saratoga Sorters.
10. Align samples at 65 KHz. Establish INV_ENR_YREM method gate (Y removal gate with ENR mode enabled) at 65 KHz Event Rate (ER).
11. Prior to sorting measure the PVR of each sample at 80 KHz and 50 KHz like standard sex sorting.

Example 6

1. Get three fresh ejaculates each from a different bull.
2. Check volume, concentration, motility, morphology and pH. Add antibiotics.
3. Remove 1 ml of ejaculate and process as with conventional semen (unsorted) procedures (25 Million/straw).
4. Standardize with extender, concentrate to 1800 million/ml.
5. Stain with Hoechst 33342 as follows:
   TUBE 0 (CONTROL): 10 ml of sperm at 160 million sperm per ml with magnetic particles (ULTRAsep).
   TUBE 1 (INV): 10 mL of sperm at 160 million sperm per ml with magnetic particles.
   TUBE 2 (INV): 10 mL of sperm at 160 million sperm per ml with magnetic particles.
   TUBE 3 (INV): 10 mL of sperm at 160 million sperm per ml with magnetic particles.
6, Incubate for 60 minutes at 34° C. Add ⅓ vol of 8% egg yolk TALP based media to each aliquot.
7. Apply the magnetic separation system for 10 minutes.
8. Transfer TUBE 0 to 4 mL sample tubes.

9. Align samples at 40 KHz. Prior to sorting measure the PVR of each sample at 40 KHz.

10. Sex sort (40 KHz, 65% X purity) sperm into 7.0 ml of Tris based media to a final of 40 ml using sheath fluid (1 catch tube per bull=3 pre-weighted tubes total) on flow cytometer.

11. Transfer TUBES 1-3 to 15 mL Falcon tubes, centrifuge and remove an amount of supernatant to target a new concentration of 300 sperm/ml.

12. Confirm the final concentrations and place the fluid volumes into 6 mL tubes for use on flow cytometers.

13. Align samples at 61 KHz. Establish INV_ENR_YREM_DEADREM gates (Y removal and dead removal gate with ENR mode enabled) at 61 KHz ER for optimal Y removal. Regions will be established based on resolution and not to a specific percent.

14. Prior to sorting, measure the PVR of each sample at 80 KHz and 50 KHz with zoom like standard sorting.

15. Inverse sort (61 KHz) sperm into 7.0 ml of Tris based media to a final of 40 mL using sheath fluid (3 catch tubes per bull=9 pre-weighted tubes) on flow cytometer.

16. Place all catch tubes in the CoolingCastle. Cool for 30 minutes.

17. Centrifuge all tubes and decant. Calculate recovery.

18. Add freeze media for a final of 4 million (CONTROL) or 6 million (INV) sperm per ¼ cc straw.

19. Hold over-night and freeze (3 straws per treatment).

20. Perform quality control checks—0 and 3 h motility, viability (PI) and PIA (PNA). Perform purity analysis.

Figure 12:
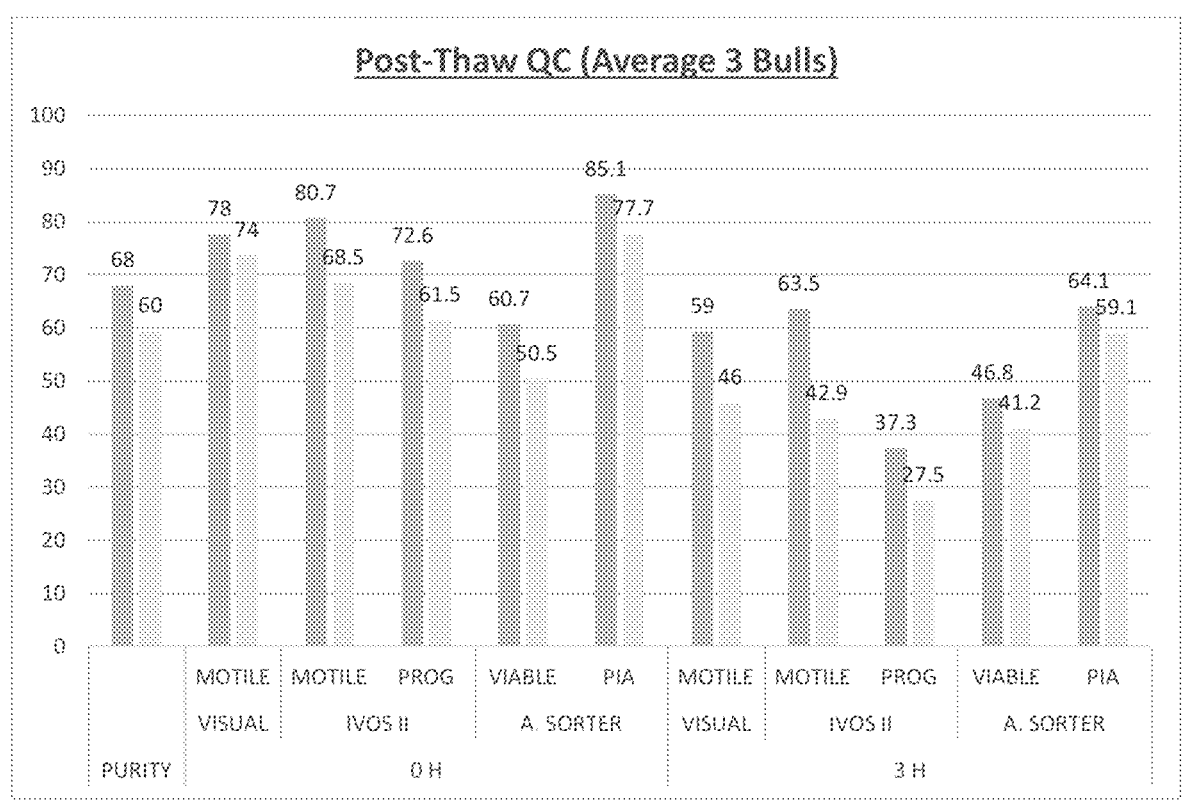
FIG. 12 is a graph showing post-thaw purity, 0-hour motility, 3-hour motility, viability and percent intact acrosomes of collected sperm achieved with the invention compared to sex-sorted sperm in which sperm of the desired sex were removed.

Results are found in Tables 11 and 12 below and in FIG. 12.

What we claim is:

1. A method of producing a subpopulation of sperm cells enriched for a sex chromosome using depletive sorting with a flow cytometer comprising:

setting the flow cytometer to an enrich (ENR) sort mode;

generating a stream containing a population of sperm cells;

interrogating the population with a source of electromagnetic radiation;

detecting signals produced in response to interrogation with the source of electromagnetic radiation at an event rate greater than 40,000 events per second;

identifying i) dead sperm cells and ii) live sperm cells in the population that do not have the sex chromosome based on the detected signals;

forming droplets from the stream at a drop drive rate, wherein the ratio of the event rate to the drop drive rate is greater than 0.85;

charging droplets comprising the identified live sperm cells in the population that do not have the sex chromosome with a charge pulse;

deflecting the charged droplets away from droplets to which a charge pulse is not applied;

collecting the droplets to which a charge pulse is not applied, wherein the collected droplets to which a charge pulse is not applied comprise i) a subpopulation of sperm cells enriched for the sex chromosome wherein the purity of the subpopulation is between about 55% and about 70% and ii) the identified dead sperm cells; and producing an insemination dosage comprising sperm cells from the collected droplets.

TABLE 11

| BULL | METHOD | PURITY | 0 H | | | | | 3 H | | | | |
| | | | VISUAL | IVOS II | | A. SORTER | | VISUAL | IVOS II | | A. SORTER | |
| | | | MOTILE | MOTILE | PROG | VIABLE | PIA | MOTILE | MOTILE | PROG | VIABLE | PIA |
| 1 | CONTROL (65% X) | 66.9 | 85 | 91.3 | 85.2 | 55.75 | *3.05 | 68 | 73.5 | 41.2 | 47.89 | 64.36 |
| | INV (Rem Y) | 58.4 | 80 | 74.7 | 69.6 | 44.24 | 73.21 | 41 | 47.8 | 24.4 | 37.3 | 56.64 |
| 2 | CONTROL (65% X) | 68.1 | 72 | 77.1 | 59.6 | 65.23 | 85.65 | 55 | 59.9 | 30.1 | 48.06 | 64.76 |
| | INV (Rem Y) | 59.6 | 71 | 64.2 | 58.2 | 53.12 | 77.77 | 47 | 35 | 18.8 | 39.95 | 56.36 |
| 3 | CONTROL (65% X) | 69.1 | 76 | 73.7 | 63 | 50.1 | 86.71 | 55 | 59.1 | 40.7 | 44.47 | 63.11 |
| | INV (Rem Y) | 60.5 | 70 | 66.5 | 56.6 | 54 | 82.23 | 50 | 46 | 39.4 | 46.24 | 64.18 |

TABLE 12

| BULL | METHOD | PURITY | 0 h Viable | 3 h Viable | Recovery Million/Tube | Sort Time Minutes | X Viable sperm sorted per minute (0 h Viable) | X Viable sperm sorted per minute (3 h Viable) |
| --- | --- | --- | --- | --- | --- | --- | --- | --- |
| 1 | BULK SORT | 67% | 56% | 48% | 25.8 | 37 | 0.26 | 0.22 |
| | INVERSE SORT | 58% | 44% | 37% | 24.0 | 12 | 0.52 | 0.44 |
| 2 | BULK SORT | 68% | 66% | 48% | 26.7 | 40 | 0.30 | 0.22 |
| | INVERSE SORT | 60% | 53% | 40% | 25.4 | 12 | 0.67 | 0.50 |
| 3 | BULK SORT | 69% | 60% | 44% | 26.2 | 35 | 0.31 | 0.23 |
| | INVERSE SORT | 61% | 54% | 46% | 24.4 | 12 | 0.67 | 0.57 |

2. The method of claim 1, wherein the step of collecting comprises collecting the subpopulation in a collector.

3. The method of claim 1, wherein the sex chromosome comprises the X chromosome.

4. The method of claim 1, wherein the sex chromosome comprises the Y chromosome.

5. The method of claim 1, wherein the collected droplets comprise between about 40% and about 45%, about 45% and about 50%, about 50% and about 55%, about 55% and about 60%, about 60% and about 65%, about 65% and about 70%, about 70% and about 75%, or about 75% and about 80%, of the population of sperm cells.

6. The method of claim 1, wherein the population of sperm cells is processed prior to the step of generating a stream by removing dead, dying or damaged sperm from the population.

7. The method of claim 1, wherein the population of sperm cells is treated with an antioxidant prior to the step of generating a stream.

8. The method of claim 1, further comprising the step of establishing a gate for sperm cells that do not have the sex chromosome.

9. The method of claim 8, wherein the gate comprises between 35% and 55% of the population of sperm cells.

10. The method of claim 1, wherein the subpopulation is collected at a rate of at least 20,000 sperm cells per second, and wherein between 40 and 80 percent of the population of sperm cells are collected.

11. The method of claim 1, further comprising the step of concentrating the population of sperm cells to a concentration of $200\times10^6$ to $400\times10^6$ sperm cells per ml prior to the step of generating a stream.

\*　\*　\*　\*　\*